US008138148B2

(12) United States Patent
Bock et al.

(10) Patent No.: US 8,138,148 B2
(45) Date of Patent: Mar. 20, 2012

(54) GDNF DERIVED PEPTIDES

(75) Inventors: Elisabeth Bock, Charlottenlund (DK); Vladimir Berezin, Kobenhavn N (DK)

(73) Assignee: Copenhagen University, København N (DK)

( * ) Notice: Subject to any disclaimer, the term of this patent is extended or adjusted under 35 U.S.C. 154(b) by 413 days.

(21) Appl. No.: 12/064,190

(22) PCT Filed: Aug. 15, 2006

(86) PCT No.: PCT/DK2006/000448
§ 371 (c)(1), (2), (4) Date: Nov. 19, 2008

(87) PCT Pub. No.: WO2007/019860
PCT Pub. Date: Feb. 22, 2007

(65) Prior Publication Data
US 2009/0221506 A1    Sep. 3, 2009

(30) Foreign Application Priority Data

Aug. 16, 2005   (DK) ................................ 2005 01153

(51) Int. Cl.
*A61K 38/18* (2006.01)
*A61K 38/16* (2006.01)
*A61K 38/03* (2006.01)
*A61K 38/04* (2006.01)

(52) U.S. Cl. ......................... 514/8.3; 514/17.7; 514/21.4

(58) Field of Classification Search .......................... None
See application file for complete search history.

(56) References Cited

FOREIGN PATENT DOCUMENTS

| WO | WO 93/06116 | | 4/1993 |
|---|---|---|---|
| WO | WO 96/40771 | * | 12/1996 |
| WO | WO 00/01815 | | 1/2000 |
| WO | WO 03/079997 | | 10/2003 |

OTHER PUBLICATIONS

Saarma M. GDNF—a stranger in the TGF-beta superfamily? Eur J Biochem. 2000; 267:6968-6971.*
Bilak MM et al. Neuroprotective utility and neurotrophic action of neurturin in postnatal motor neurons: comparison with GDNF and persephin. Mol Cell Neurosci. 1999; 13:326-336.*
Blakytny R et al. Inactivation of active and latent transforming growth factor beta by free thiols: Potential redox regulation of biological action. Int J Biochem Cell Biol. 2006; 38:1363-1373.*
Bocquet A et al. Failure of GPI compounds to display neurotrophic activity in vitro and in vivo. Eur J Pharmacol. 2001; 415:173-180.*
Corse AM et al. Preclinical testing of neuroprotective neurotrophic factors in a model of chronic motor neuron degeneration. Neurobiol Disease. 1999; 6:335-346.*
Ho TW et al. TGFbeta trophic factors differentially modulate motor axon outgrowth and protection from excitotoxicity. Exp Neurol. 2000; 161:664-675.*
Nielsen J et al. Role of glial cell line-derived neurotrophic factor (GDNF)-neural cell adhesion molecule (NCAM) interactions in induction of neurite outgrowth and identification of a binding site for NCAM in the heel region of GDNF. J Neurosci. Sep. 2009; 29(36):11360-11376.*
Peterson AL et al.Treatment of Parkinson's disease with trophic factors. Neurotherapeutics, Apr. 2008; 5:270-280.*
Airaksinen MS, Saarma M. The GDNF family: signalling, biological functions and therapeutic value. Nat Rev Neurosci. 2002;3:383-94.
Arenas et al. GDNF prevents degeneration and pro-motes the phenotype of brain noradrenergic neurons in vivo. Neuron. 1995;15:1465-73.
Baloh RH, et al. Artemin, a novel member of the GDNF ligand family, supports peripheral and central neurons and signals through the GFRa3-RET receptor complex. Neuron, 1998;21:1291-302.
Baloh RH, et al. Functional mapping of receptor specificity domains of glial cell line-derived neurotrophic factor (GDNF) family ligands and production of GFRa1 RET-specific agonists. J Biol Chem. 2000;275:3412-20.
C. Geetha et al. J Dent Research, 84(2), pp. 149-153, 2005.
Eketjäll S, et al. Distinct structural elements in GDNF mediate binding to GFRa1 and activation of the GFRa1-c-Ret receptor com-plex. EMBO J. 19991;18:5901-10.
Hearn CJ, Murphy M, Newgreen D. GDNF and ET-3 differentially modulate the numbers of avian enteric neural crest cells and enteric neurons in vitro. Dev Biol. 1998;197:93-105.
Kotzbauer PT, et al. J. Neurturin, a relative of glial-cell-line-derived neurotrophic factor. Na-ture. 1996;384:467-70.
Lin LF, et al. GDNF: a glial cell line-derived neurotrophic factor for midbrain dopaminergic neurons. Science. 1993;260:1130-2.
Milbrandt J, et al. Persephin, a novel neurotrophic factor related to GDNF and neurturin. Neuron. 1998;20:245-53.
Paratcha G, et al. The neural cell adhesion molecule NCAM is an alternative signaling receptor for GDNF family ligands. Cell, vol. 113, 2003, 867-79.
Rønn LC, et al. A simple procedure for quantification of neurite outgrowth based on stereological prin-ciples. J Neurosci Methods. 2000;100:25-32.
Saarma M, Sariola H. Other neurotrophic factors: glial cell line-derived neurotrophic factor (GDNF). Microsc Res Tech. 1999:45:292-302.
Yan H, et al. Developmental changes in neurite outgrowth re-sponses of dorsal root and sympathetic ganglia to GDNF, neurturin, and artemin. Dev Dyn. 2003;227:395-401.

\* cited by examiner

*Primary Examiner* — Elizabeth C Kemmerer
*Assistant Examiner* — Kimberly A Ballard
(74) *Attorney, Agent, or Firm* — Iver P. Cooper

(57) ABSTRACT

The present invention relates to peptide fragments derived from the proteins belonging to the TGFbeta superfamily, pharmaceutical compositions comprising these peptide fragments and uses thereof for treatment of a disease or condition wherein the effects of stimulating neuronal cell differentiation, neuronal cell survival, stimulating neural plasticity associated with learning and memory and/or inhibiting inflammatory response are beneficial for treatment.

52 Claims, 38 Drawing Sheets

SEQUENCE LISTING

```
<160> NUMBER OF SEQ ID NOS: 25

<210> SEQ ID NO 1
<211> LENGTH: 15
<212> TYPE: PRT
<213> ORGANISM: Homo sapiens

<400> SEQUENCE: 1

Leu Asn Val Thr Asp Leu Gly Leu Gly Tyr Glu Thr Lys Glu Glu
1               5                   10                  15

<210> SEQ ID NO 2
<211> LENGTH: 15
<212> TYPE: PRT
<213> ORGANISM: Homo sapiens

<400> SEQUENCE: 2

Val Pro Val Arg Ala Leu Gly Leu Gly His Arg Ser Asp Glu Leu
1               5                   10                  15

<210> SEQ ID NO 3
<211> LENGTH: 15
<212> TYPE: PRT
<213> ORGANISM: Homo sapiens

<400> SEQUENCE: 3

Val Arg Val Ser Glu Leu Gly Leu Gly Tyr Ala Ser Asp Glu Thr
```

```
                1               5                  10                 15
```

<210> SEQ ID NO 4
<211> LENGTH: 15
<212> TYPE: PRT
<213> ORGANISM: Homo sapiens

<400> SEQUENCE: 4

```
Leu Ser Val Ala Glu Leu Gly Leu Gly Tyr Ala Ser Glu Glu Lys
1               5                  10                 15
```

<210> SEQ ID NO 5
<211> LENGTH: 17
<212> TYPE: PRT
<213> ORGANISM: Homo sapiens

<400> SEQUENCE: 5

```
Ile Asp Phe Arg Lys Asp Leu Gly Trp Lys Trp Ile His Glu Pro Lys
1               5                  10                 15

Gly
```

<210> SEQ ID NO 6
<211> LENGTH: 17
<212> TYPE: PRT
<213> ORGANISM: Homo sapiens

<400> SEQUENCE: 6

```
Ile Asp Phe Lys Arg Asp Leu Gly Trp Lys Trp Ile His Glu Pro Lys
1               5                  10                 15

Gly
```

<210> SEQ ID NO 7
<211> LENGTH: 17
<212> TYPE: PRT
<213> ORGANISM: Homo sapiens

<400> SEQUENCE: 7

```
Ile Asp Phe Arg Gln Asp Leu Gly Trp Lys Trp Val His Glu Pro Lys
1               5                  10                 15

Gly
```

<210> SEQ ID NO 8
<211> LENGTH: 18
<212> TYPE: PRT
<213> ORGANISM: Homo sapiens

<400> SEQUENCE: 8

```
Ile Asp Leu Gln Gly Met Lys Trp Ala Lys Asn Trp Val Leu Glu Pro
1               5                  10                 15

Pro Gly
```

<210> SEQ ID NO 9
<211> LENGTH: 15
<212> TYPE: PRT
<213> ORGANISM: Homo sapiens

<400> SEQUENCE: 9

```
Glu Thr Thr Tyr Asp Lys Ile Leu Lys Asn Leu Ser Arg Asn Arg
1               5                  10                 15
```

<210> SEQ ID NO 10
<211> LENGTH: 15
<212> TYPE: PRT

<213> ORGANISM: Homo sapiens

<400> SEQUENCE: 10

Arg Ser Pro His Asp Leu Ser Leu Ala Ser Leu Leu Gly Ala Gly
1               5                   10                  15

<210> SEQ ID NO 11
<211> LENGTH: 15
<212> TYPE: PRT
<213> ORGANISM: Homo sapiens

<400> SEQUENCE: 11

Ala Arg Val Tyr Asp Leu Gly Leu Arg Arg Leu Arg Gln Arg Arg
1               5                   10                  15

<210> SEQ ID NO 12
<211> LENGTH: 15
<212> TYPE: PRT
<213> ORGANISM: Homo sapiens

<400> SEQUENCE: 12

Arg Thr Gln His Gly Leu Ala Leu Ala Arg Leu Gln Gly Gln Gly
1               5                   10                  15

<210> SEQ ID NO 13
<211> LENGTH: 15
<212> TYPE: PRT
<213> ORGANISM: Homo sapiens

<400> SEQUENCE: 13

Trp Ser Leu Asp Thr Gln Tyr Ser Lys Val Leu Ala Leu Tyr Asn
1               5                   10                  15

<210> SEQ ID NO 14
<211> LENGTH: 15
<212> TYPE: PRT
<213> ORGANISM: Homo sapiens

<400> SEQUENCE: 14

Trp Ser Ser Asp Thr Gln His Ser Arg Val Leu Ser Leu Tyr Asn
1               5                   10                  15

<210> SEQ ID NO 15
<211> LENGTH: 15
<212> TYPE: PRT
<213> ORGANISM: Homo sapiens

<400> SEQUENCE: 15

Arg Ser Ala Asp Thr Thr His Ser Thr Val Leu Gly Leu Tyr Asn
1               5                   10                  15

<210> SEQ ID NO 16
<211> LENGTH: 12
<212> TYPE: PRT
<213> ORGANISM: Homo sapiens

<400> SEQUENCE: 16

Asp Asp Leu Ser Phe Leu Asp Asp Asn Leu Val Tyr
1               5                   10

<210> SEQ ID NO 17
<211> LENGTH: 12
<212> TYPE: PRT
<213> ORGANISM: Homo sapiens

<400> SEQUENCE: 17

Glu Ala Val Ser Phe Met Asp Val Asn Ser Thr Trp
1               5                   10

<210> SEQ ID NO 18
<211> LENGTH: 12
<212> TYPE: PRT
<213> ORGANISM: Homo sapiens

<400> SEQUENCE: 18

Asp Glu Val Ser Phe Leu Asp Ala His Ser Arg Tyr
1               5                   10

<210> SEQ ID NO 19
<211> LENGTH: 12
<212> TYPE: PRT
<213> ORGANISM: Homo sapiens

<400> SEQUENCE: 19

Asp Val Ala Phe Leu Asp Arg His Arg Trp Gln
1               5                   10

<210> SEQ ID NO 20
<211> LENGTH: 12
<212> TYPE: PRT
<213> ORGANISM: Homo sapiens

<400> SEQUENCE: 20

Glu Pro Leu Pro Ile Val Tyr Tyr Val Gly Arg Lys
1               5                   10

<210> SEQ ID NO 21
<211> LENGTH: 12
<212> TYPE: PRT
<213> ORGANISM: Homo sapiens

<400> SEQUENCE: 21

Glu Pro Leu Thr Ile Leu Tyr Tyr Ile Gly Lys Thr
1               5                   10

<210> SEQ ID NO 22
<211> LENGTH: 12
<212> TYPE: PRT
<213> ORGANISM: Homo sapiens

<400> SEQUENCE: 22

Glu Pro Leu Thr Ile Leu Tyr Tyr Val Gly Arg Thr
1               5                   10

<210> SEQ ID NO 23
<211> LENGTH: 11
<212> TYPE: PRT
<213> ORGANISM: Homo sapiens

<400> SEQUENCE: 23

Asp Leu Ser Phe Leu Asp Asp Asn Leu Val Tyr
1               5                   10

<210> SEQ ID NO 24
<211> LENGTH: 11
<212> TYPE: PRT
<213> ORGANISM: Homo sapiens

<400> SEQUENCE: 24

Val Ser Phe Met Asp Val Asn Ser Thr Trp Arg
1               5                   10

```
<210> SEQ ID NO 25
<211> LENGTH: 11
<212> TYPE: PRT
<213> ORGANISM: Homo sapiens

<400> SEQUENCE: 25

Glu Val Ser Phe Leu Asp Ala His Ser Arg Tyr
1               5                   10
```

GDNF DERIVED PEPTIDES

FIELD OF INVENTION

The present invention relates to peptide fragments derived from the proteins belonging to the TGFbeta superfamily, pharmaceutical compositions comprising said peptide fragments and uses thereof for treatment of a disease or condition wherein the effects of stimulating neuronal cell differentiation, neuronal cell survival, stimulating neural plasticity associated with learning and memory and/or inhibiting inflammatory response are beneficial for treatment.

BACKGROUND OF INVENTION

GDNF was originally purified, and characterized in the early 1990's as a neurotrophic factor supporting the survival and differentiation of midbrain dopaminergic neurons, and on the basis of the amino acid sequence of GDNF, it was possible to clone the GDNF gene (Lin et al., 1993). Neurturin (NRTN, also known as NTN) was isolated in 1996 based on its ability to promote survival of sympathetic neurons (Kotzbauer et al., 1996). Subsequently, persephin (PSPN, also known as PSP) and artemin (ARTN, also known as ART), were cloned on the basis of sequence homology (Milbrandt et al., 1998; Baloh et al., 1998). Reportedly, analysis of the Genome Database has indicated the unlikelihood of finding other functional GDNF family ligands (GFLs) (Airaksinen & Saarma, 2002).

A variety of biological actions have been ascribed to the GFLs. NRTN, PSPN, and ARTN, like GDNF, promote survival of midbrain dopaminergic neurons (Lin et al., 1993; Milbrandt et al., 1998; Baloh et al., 1998a). The survival of several other neuronal subpopulations in the CNS is supported by the GFLs, including central motorneurons (Milbrandt et al., 1998) and noradrenergic neurons (Arenas et al., 1995). GDNF, NRTN, and ARTN also support the survival of neurons in the PNS, including sympathetic, parasympathetic, sensory (Kotzbauer et al., 1996; Baloh et al., 1998), and enteric neurons (Hearn et al., 1998). In addition to their survival promoting effects, the GFLs also promotes neuronal differentiation (Lin et al., 1993; Baloh et al., 1998a; Yan et al., 2003; Paratcha et al., 2003).

As typical for secreted proteins, the four members of the GDNF-family are synthesized as inactive prepro-forms. The signal peptide is cleaved from the prepro-form of GDNF, and proGDNF is secreted. Further cleavage turns proGDNF into the 134 amino acid-long mature GDNF. Mature NRTN contains 100 amino acids, mature PSPN consists of 96 amino acids, and mature ARTN contains 113 amino acids (Kotzbauer et al., 1996; Milbrandt et al., 1998; Baloh et al., 1998). The GFLs are quite homologous, sharing from 53 to 64% sequence similarity. The identity of the protease(s) cleaving pro-GFLs to mature GFLs has yet to be determined.

The sequences of the four GFLs reveal the existence of seven conserved cysteine residues within the mature proteins. These residues are spaced in a similar manner as the seven conserved cysteine residues found in members of the transforming growth factor (TGF)-β superfamily. Hence, although they show less than 20% sequence similarity with the other members of the family, the GFLs are considered to be members of the TGF-β superfamily, constituting their own subfamily (Lin et al., 1993; Kotzbauer et al, 1996; Milbrandt et al., 1998; Baloh et al., 1998). All members of the TGF-β superfamily belong to the cysteine knot growth factor superfamily (Saarma & Sariola, 1999). The proteins in this family are characterized by being dimeric proteins containing a topological knot formed by three cysteine residues. Together with adjacent amino acids two of these cysteine residues form a covalent ring, through which the third cysteine passes.

Possible GFRα binding sites in GDNF have been investigated in two studies (Eketjäll et al., 1999; Baloh et al., 2000). The first study identified three negatively charged amino acids in finger 1 and one in finger 2, which are critical for binding of GDNF to GFRα1 (Eketjäll et al., 1999). These residues are placed in the most distal part of the fingers, as are four hydrophobic amino acids (one in finger 1, the rest in finger 2) also shown to be crucial for binding of GDNF to GFRα1. In addition, the flexible N-terminal region of GDNF is indicated to be of importance for binding to GFRα1. In contrast, the positively charged amino acids concentrated in the heel, did not appear to be involved in binding to GFRα1 (Eketjäll et al., 1999). Surprisingly, neither one of the identified residues in finger 2 nor one of the hydrophobic residues in finger 1 were required for GDNF binding in the presence of Ret since GDNF molecules mutated at these positions were still able to induce phosphorylation of Ret. Deletion of the N-terminal region did not inhibit Ret phosphorylation either. The authors therefore proposed the existence of two distinct binding sites for GDNF in GFRα1. One binding site consisting of GFRα1 receptors alone would be used for binding GDNF in the absence of Ret, while another binding site consisting of residues from GFRα1 and Ret would come into play, when GDNF interacts with a preassociated GFRα1-Ret complex (Eketjäll et al., 1999).

In the study by Baloh et al. (2000), it was found that two regions in finger 2 were important for GDNF-induced activation of Ret through GFRα1, whereas the flexible N-terminal was not required. Similar experiments showed that the corresponding two regions in NRTN and ARTN were important for the ability of these GFLs to activate Ret through GFRα2 and GFRα3, respectively. For NRTN and ARTN, regions comprising the most N-terminal part of the large α-helix were also required for Retactivation (Baloh et al., 2000).

In summary, the existence of more than one binding site in GFLs is indicated from the two studies, and although there appears to be some discrepancy about which finger is most important, the works of Eketjäll et al. (1999) and Baloh et al. (2000) underline the importance of the finger regions in binding of GDNF to its receptor complex and subsequent activation of Ret.

The understanding of the heterophilic interaction between NCAM and GDNF/GFRα1 is still very limited, but studies have indicated that both GDNF and GFRα1 bind to NCAM, and that the binding of NCAM to GDNF is greatly potentiated in the presence of GFRα1 (Paratcha et al., 2003). Furthermore, in the same study it was suggested that the GDNF-induced neurite outgrowth occurs independently of the FGFR and probably also independently of trans homophilic NCAM interactions. The GDNF-GFRα-NCAM interaction in fact seemed to interfere with homophilic NCAM interactions (Paratcha et al., 2003).

REFERENCES

Airaksinen M S, Saarma M. The GDNF family: signalling, biological functions and therapeutic value. Nat Rev Neurosci. 2002; 3:383-94.

Arenas E, Trupp M, Åkerud P, Ibáñez C F. GDNF prevents degeneration and promotes the phenotype of brain noradrenergic neurons in vivo. Neuron. 1995; 15:1465-73.

Baloh R H, Tansey M G, Lampe P A, Fahrner T J, Enomoto H, Simburger K S, Leitner M L, Araki T, Johnson E M Jr, Milbrandt J. Artemin, a novel member of the GDNF ligand family, supports peripheral and central neurons and signals through the GFRα3—RET receptor complex. Neuron. 1998; 21:1291-302.

Baloh R H, Tansey M G, Johnson E M Jr, Milbrandt J. Functional mapping of receptor specificity domains of glial cell line-derived neurotrophic factor (GDNF) family ligands and production of GFRα1 RET-specific agonists. J Biol. Chem. 2000; 275:3412-20.

Eketjäll S, Fainzilber M, Murray-Rust J, Ibáñez CF. Distinct structural elements in GDNF mediate binding to GFRα1 and activation of the GFRα1-c-Ret receptor complex. EMBO J. 19991; 18:5901-10.

Hearn C J, Murphy M, Newgreen D. GDNF and ET-3 differentially modulate the numbers of avian enteric neural crest cells and enteric neurons in vitro. Dev Biol. 1998; 197:93-105.

Kotzbauer P T, Lampe P A, Heuckeroth R O, Golden J P, Creedon D J, Johnson E M Jr, Milbrandt J. Neurturin, a relative of glial-cell-line-derived neurotrophic factor. Nature. 1996; 384:467-70.

Lin L F, Doherty D H, Lile J D, Bektesh S, Collins F. GDNF: a glial cell line-derived neurotrophic factor for midbrain dopaminergic neurons. Science. 1993; 260:1130-2.

Milbrandt J, de Sauvage F J, Fahrner T J, Baloh R H, Leitner M L, Tansey M G, Lampe P A, Heuckeroth R O, Kotzbauer P T, Simburger K S, Golden J P, Davies J A, Vejsada R, Kato A C, Hynes M, Sherman D, Nishimura M, Wang L C, Vandlen R, Moffat B, Klein R D, Poulsen K, Gray C, Garces A, Johnson E M Jr, et al. Persephin, a novel neurotrophic factor related to GDNF and neurturin. Neuron. 1998; 20:245-53.

Paratcha G, Ledda F, Ibáñez CF. The neural cell adhesion molecule NCAM is an alternative signaling receptor for GDNF family ligands. Cell. 2003; 113:867-79.

Rønn LC, Ralets I, Hartz B P, Bech M, Berezin A, Berezin V, Moller A, Bock E. A simple procedure for quantification of neurite outgrowth based on stereological principles. J Neurosci Methods. 2000; 100:25-32.

Saarma M, Sariola H. Other neurotrophic factors: glial cell line-derived neurotrophic factor (GDNF). Microsc Res Tech. 1999; 45:292-302.

Yan H, Newgreen D F, Young H M. Developmental changes in neurite outgrowth responses of dorsal root and sympathetic ganglia to GDNF, neurturin, and artemin. Dev Dyn. 2003; 227:395-401.

SUMMARY OF THE INVENTION

The present invention discloses short peptide fragments of proteins belonging to the TGFbeta superfamily, in particular GDNF, NRTN, PSPN, ARTN, TGFbeta-1, TGFbeta-2, TGFbeta-3 and TGFbeta-4, capable of stimulating neuronal cell differentiation, neuronal cell survival and neural plasticity associated with learning and memory and capable of inhibiting of inflammatory response. According to the invention, all the peptide fragments described herein are structurally similar, namely they comprise a common amino acid motif which is a prerequisite for biological activity of the peptides.

Thus, in the first aspect the present invention relates to a peptide having a sequence of 6 to 22 contiguous amino acid residues comprising the motif of the formula:

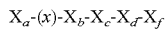

wherein
$X_a$ is amino acid residue D, E, A or G, (x) is a sequence of 2-3 amino acid residues or a single amino acid residue selected from the group consisting of amino acid residues A, D, E, G, I, K, L, P, Q, S, T and V,
$X_b$ is amino acid residue Y or H, or a hydrophobic amino acid residue, and
at least one of $X_c$, $X_d$ or $X_f$ is a charged or hydrophobic amino acid residue.

The invention discloses particular peptide sequences derived from GDNF, NRTN, PSPN, ARTN, TGFbeta-1, TGFbeta-2, TGFbeta-3 and TGFbeta-4, which all comprise the motif of the above and are capable of stimulating neuronal cell differentiation, neuronal cell survival and/or neural plasticity associated with learning and memory.

Further, the invention relates to a compound comprising a peptide sequence the motif of the above, in particular a compound comprising a sequence derived from GDNF, NRTN, PSPN, ARTN, TGFbeta-1, TGFbeta-2, TGFbeta-3 or TGFbeta-4.

Then, the invention relates to uses of disclosed peptide sequences and compounds comprising thereof for the manufacture of a medicament and/or for the production of an antibody. The invention also relates to pharmaceutical compositions comprising peptides, compounds and/or antibodies of the invention.

Methods of stimulating of neurite cell differentiation, neuronal cell survival and/or neuronal plasticity associated with learning and memory comprising using peptides, compounds, antibodies and/or pharmaceutical compositions of the invention are also in the scope of the protection, as well as methods of treatment comprising administering to an individual in need an effective amount of a peptide, compound, antibody or pharmaceutical composition of the invention.

C3d is a positive control (the peptide which is increase the survival of dopaminergic neurons, see Ditlevsen et al., J. Neurochem., 2003).

Figure 1:
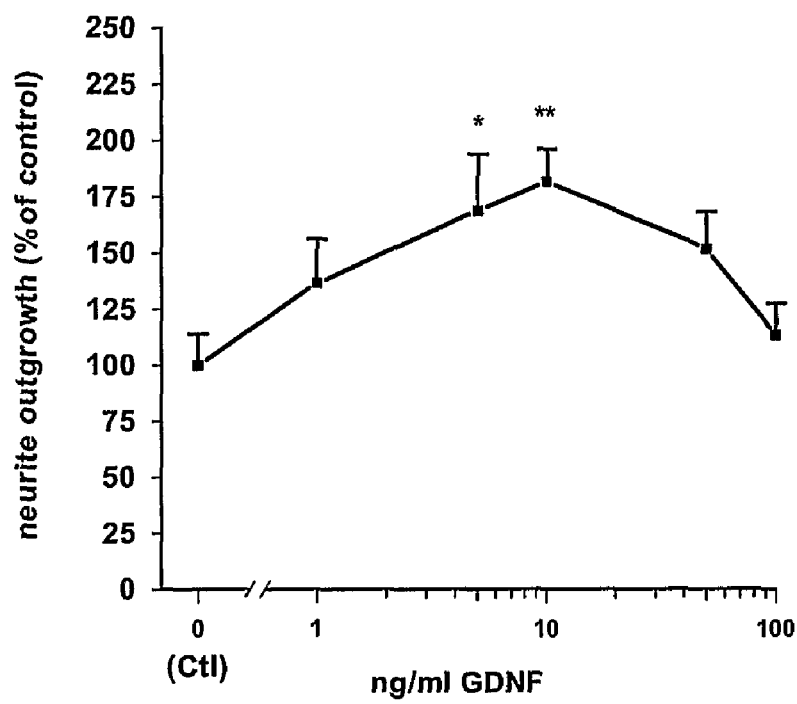
FIG. 1: GDNF-induced neurite outgrowth in primary hippocampal neurons. Cells were stimulated with GDNF (1, 5, 10, 50, and 100 ng/ml) for 24 hours. Neurons grown in medium alone served as control. For the control absolute length of neurite outgrowth was 11.65 μm±1.57 μm. Results are expressed as percentage of control and presented as means±S.E.M. The figure is based on results from 5 independent experiments. The mean neurite outgrowth lengths were compared using one-way ANOVA for repeated measurements. $F_{(5, 24)}=5.903$, $p<0.01$, shows that there is an overall statistically significant effect of GDNF-treatment.
Figure 2:
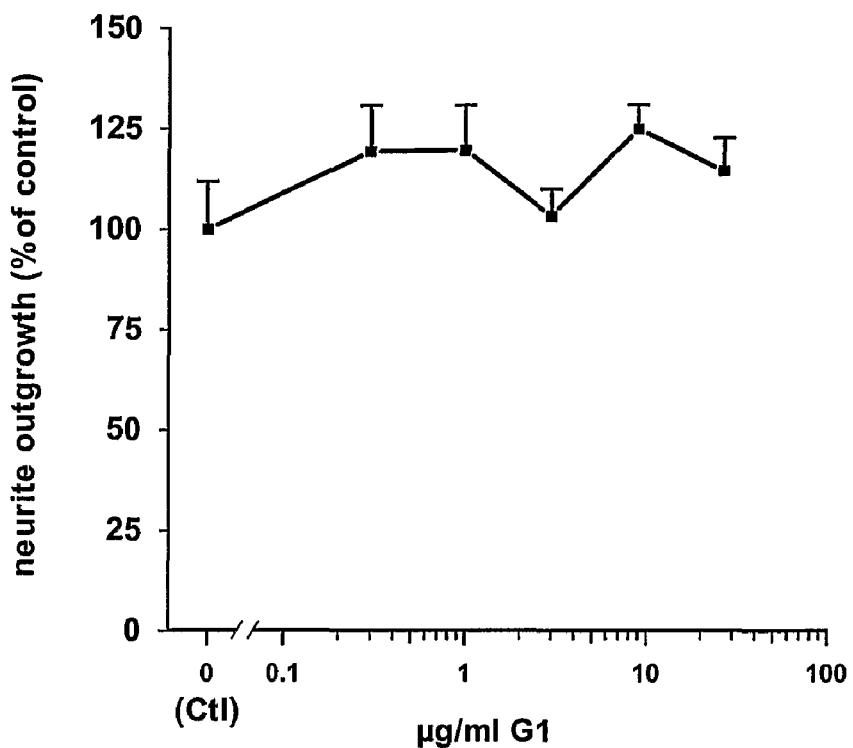
FIG. 2: G1 does not induce neurite outgrowth in primary hippocampal neurons. Cells were stimulated with (G1 (0.3, 1, 3, 9, and 27 μg/ml) for 24 hours. Neurons grown in medium alone served as control. For controls absolute length of neurite outgrowth was 11.68 μm±2.20 μm (A) or 11.00 μm±0.94 μm (B). Results are expressed as percentage of control and presented as means±S.E.M. The figure is based on results from 5 (A) or 4 (B) independent experiments. The mean neurite outgrowth lengths were compared using one-way ANOVA for repeated measurements. $F_{(5, 24)}=0.4873$, $p=0.7823$, shows that the overall effect of G1-treatment is not statistical significant.
Figure 3:
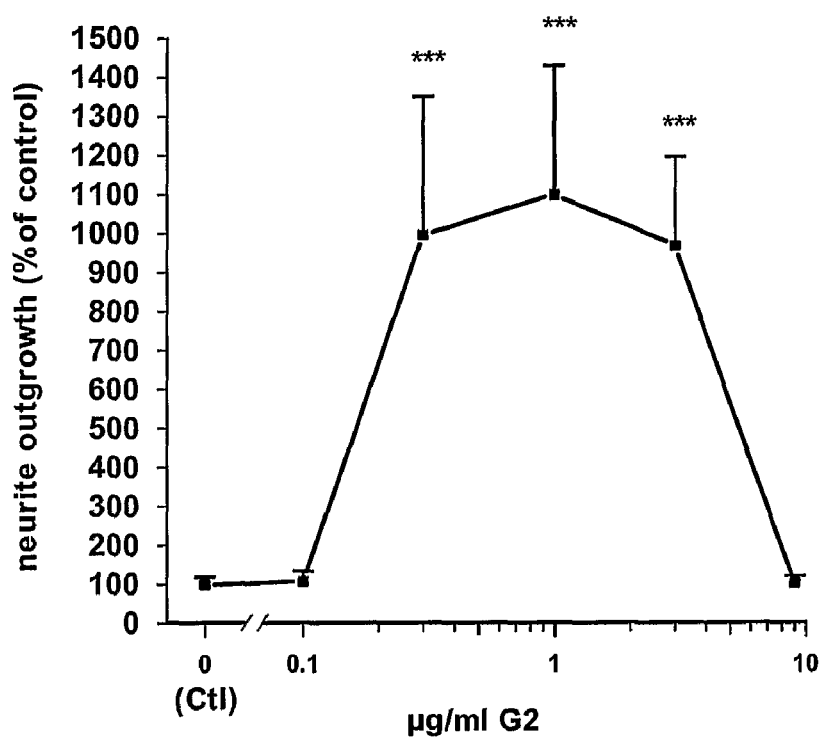
FIG. 3: G2-induced neurite outgrowth in primary hippocampal neurons. Cells were stimulated with G2 (0.1, 0.3, 1, 3, and 9 μg/ml) for 24 hours. Neurons grown in medium alone served as control. For controls absolute length of neurite outgrowth was 11.50 μm±2.20 μm. Results are expressed as percentage of control and presented as means±S.E.M. The figure is based on results from 4 independent experiments. The mean neurite outgrowth lengths were compared using one-way ANOVA for repeated measurements. $F_{(5, 18)}=91.91$, p<0.0001, shows that there is an overall statistical significant effect of G2-treatment. The effect of individual concentrations of G2 was compared to control using post-testing with Tukeys multiple comparisons test.
Figure 4:
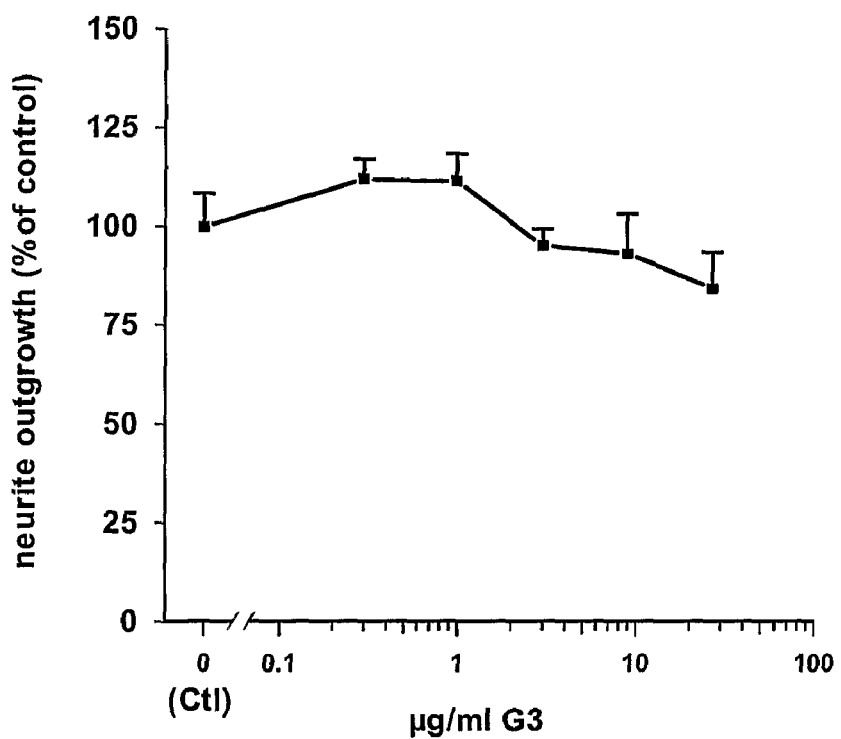
FIG. 4: G3 do not induce neurite outgrowth in primary hippocampal neurons. Cells were stimulated with G3 (0.3, 1, 3, 9, and 27 μg/ml) for 24 hours. Neurons grown in medium alone served as control. For controls absolute length of neurite outgrowth was 11.68 μm±2.20 μm (A) or 11.00 μm+0.94 μm (B). Results are expressed as percentage of control and presented as means±S.E.M. The figure is based on results from 5 (A) or 4 (B) independent experiments. The mean neurite outgrowth lengths were compared using one-way ANOVA for repeated measurements. $F_{(5, 18)}=1.710$, p=0.1833, shows that the overall effect of G3-treatment is not statistical significant.
Figure 5:
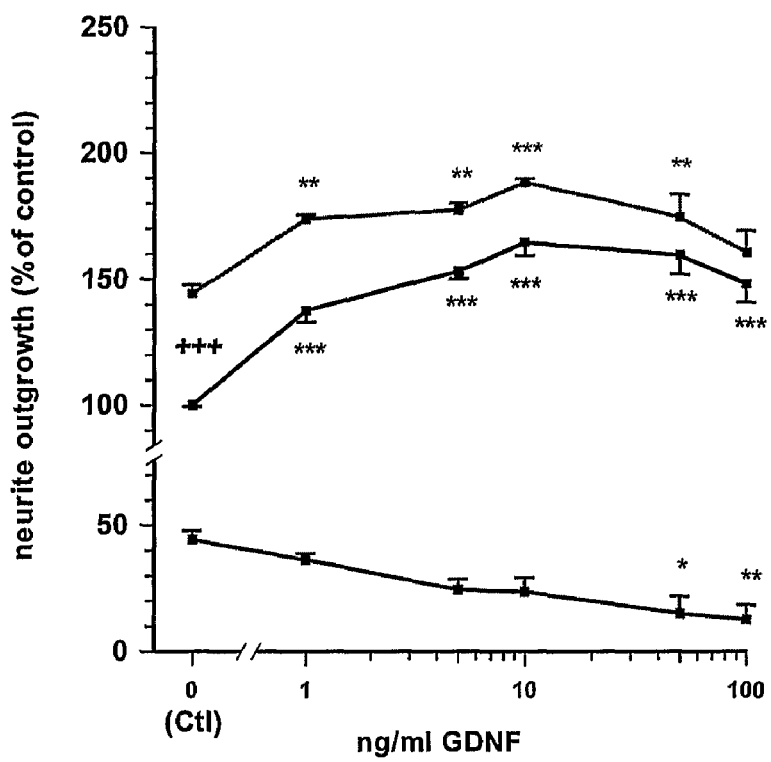
FIG. 5: GDNF-induced neurite outgrowth in hippocampal neurons grown in co-culture with control fibroblasts or NCAM-expressing fibroblasts. Neurons were grown on top of either control fibroblasts (middle curve) or NCAM-expressing fibroblasts (upper curve) and stimulated with GDNF (1, 5, 10, 50, and 100 ng/ml) for 24 hours. Neurons grown in medium alone (lower curve) served as controls. Results are expressed as percentage of control (non-stimulated neurons on control fibroblasts) and presented as means±S.E.M. For controls on control fibroblasts absolute length of neurite outgrowth was 38.97 μm±0.21 μm. The figure is based on results from 4 independent experiments. The mean neurite outgrowth lengths were compared using separate one-way ANOVAs for repeated measurements. $F_{(5, 18)}=27.33$, p<0.0001, shows that there is an overall significant effect of GDNF-treatment for neurons grown on control fibroblasts. $F_{(5, 18)}=9.967$, p<0.001 shows that there is an overall significant effect of GDNF-treatment for neurons grown on NCAM-expressing fibroblasts. The effect of individual concentrations of GDNF was compared to the matching control using post-testing with Tukeys multiple comparisons test. * beside middle curve indicates p-values for comparison to non-stimulated cells grown on control fibroblasts, whereas * beside upper curve indicates p-values for comparison to non-stimulated cells grown on NCAM-expressing fibroblasts. The two controls were compared using a paired t-test, which showed that they are statistically significantly different (p-value indicated by + beside middle curve). For each concentration the difference between neurite outgrowth in neurons grown on control fibroblasts and in neurons grown on NCAM-expressing fibroblasts was calculated and expressed as percentage of control (non-stimulated neurons on control fibroblasts (blue curve). One-way ANOVA for repeated measurements showed that the mean differences are not all the same (F(5, 18)=5.835, p<0.05). The difference at individual concentrations of GDNF was compared to the difference of the two matching controls (the NCAM-mediated neurite outgrowth) using post-testing with Tukeys multiple comparisons test. * beside lower curve indicates p-values.
Figure 6:
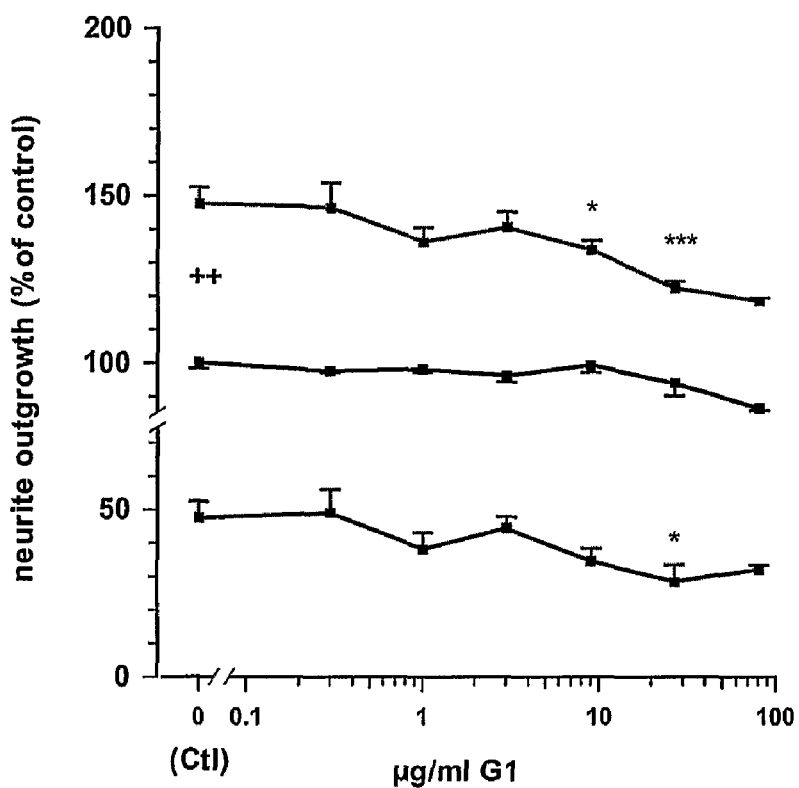
FIG. 6: G1 interferes with NCAM-induced neurite outgrowth in hippocampal neurons grown in co-culture with control fibroblasts or NCAM-expressing fibroblasts. Neurons were grown on top of either control fibroblasts (middle curve) or NCAM-expressing fibroblasts (upper curve) and stimulated with (G1 (0.3, 1, 3, 9, 27 and 81 μg/ml) for 24 hours. Neurons grown in medium alone lower curve served as controls. Results are expressed as percentage of control (non-stimulated neurons on control fibroblasts) and presented as means±S.E.M. For controls on control fibroblasts absolute length of neurite outgrowth was 34.64 μm±0.63 μm for. The figure is based on results from 4 independent experiments. The mean neurite outgrowth lengths were compared using separate one-way ANOVAs for repeated measurements. $F_{(4, 15)}=1.581$, p=0.2422, shows that there is no overall significant effect of G1-treatment for neurons grown on control fibroblasts. $F_{(4, 15)}=10.45$, p<0.001 shows that there is an overall statistical significant effect of G1-treatment for neurons grown on NCAM-expressing fibroblasts. This effect seems to be inhibitory at higher concentrations of G1. The effect of individual concentrations of G1 was compared to the matching control using post-testing with Tukeys multiple comparisons test. * beside upper curve indicates p-values for comparison to non-stimulated cells grown on NCAM-expressing fibroblasts. The two controls were compared using a paired t-test, which showed that they are statistically significant different (p-value indicated by + beside middle curve). For each concentration the difference between neurite outgrowth in neurons grown on control fibroblasts and in neurons grown on NCAM-expressing fibroblasts was calculated and expressed as percentage of control (non-stimulated neurons on control fibroblasts) (lower curve). One-way ANOVA for repeated measurements showed that the mean differences are not all the same ($F_{(4, 15)}=3.389$, p<0.05). The difference at individual concentrations of GDNFp2 was compared to the difference of the two controls using post-testing with Tukeys multiple comparisons test. * beside lower curve indicates p-values.
Figure 7:
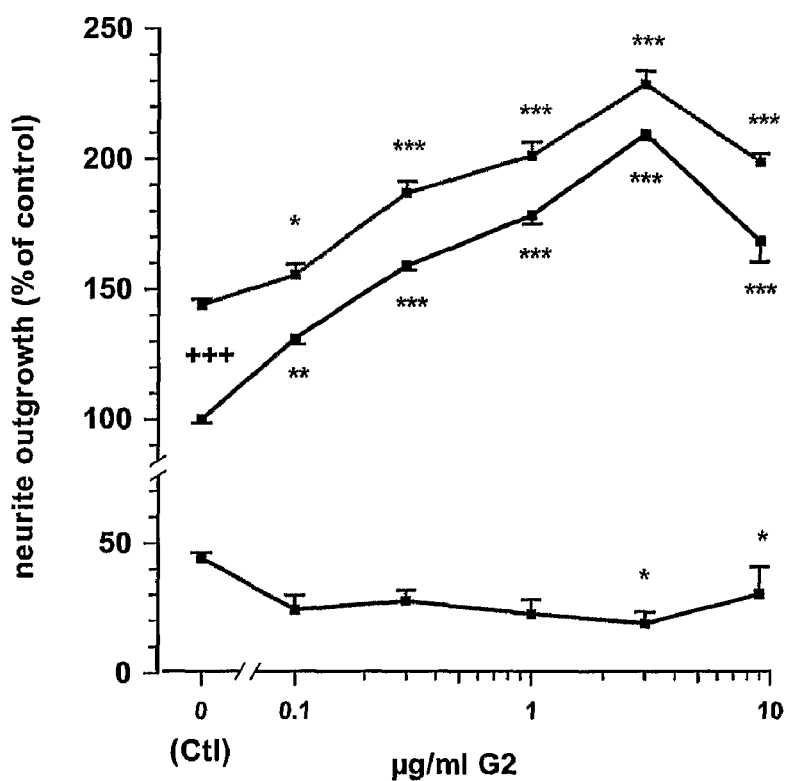
FIG. 7: G2-induced neurite outgrowth in hippocampal neurons grown in co-culture with control fibroblasts or NCAM-expressing fibroblasts. Neurons were grown on top of either control fibroblasts (middle curve) or NCAM-expressing fibroblasts (upper curve) and stimulated with (G2 (0.1, 0.3, 1, 3, and 9 μg/ml) for 24 hours. Neurons grown in medium alone (lower curve) served as controls. Results are expressed as percentage of control (non-stimulated neurons on control fibroblasts) and presented as means±S.E.M. For controls on control fibroblasts absolute length of neurite outgrowth was 38.74 μm±0.47 μm for. The figure is based on results from 4 independent experiments. The mean neurite outgrowth lengths were compared using separate one-way ANOVAs for repeated measurements. $F_{(5, 18)}=81.76$, p<0.0001, shows that there is an overall significant effect of G2-treatment for neurons grown on control fibroblasts. $F_{(5, 18)}=176.6$, p<0.0001 shows that there is an overall significant effect of G2-treatment for neurons grown on NCAM-expressing fibroblasts The effect of individual concentrations of G2 was compared to the matching control using post-testing with Tukeys multiple comparisons test. * beside middle curve indicates p-values for comparison to non-stimulated cells grown on control fibroblasts, whereas * beside upper curve indicates p-values for comparison to non-stimulated cells grown on NCAM-expressing fibroblasts. The two controls were compared using a paired t-test, which showed that they are statistically significantly different (p-value indicated by + beside middle curve). For each concentration the difference between neurite outgrowth in neurons grown on control fibroblasts and in neurons grown on NCAM-expressing fibroblasts was calculated and expressed as percentage of control (non-stimulated neurons on control fibroblasts) (blue curve). One-way ANOVA for repeated measurements showed that the mean differences are not all the same ($F_{(5, 18)}=3.761$, p<0.05 for). The difference at individual concentrations of GDNF or GDNFp1 was compared to the difference of the two matching controls (the NCAM-mediated neurite outgrowth) using post-testing with Tukeys multiple comparisons test. * beside lower curve indicates p-values.
Figure 8:
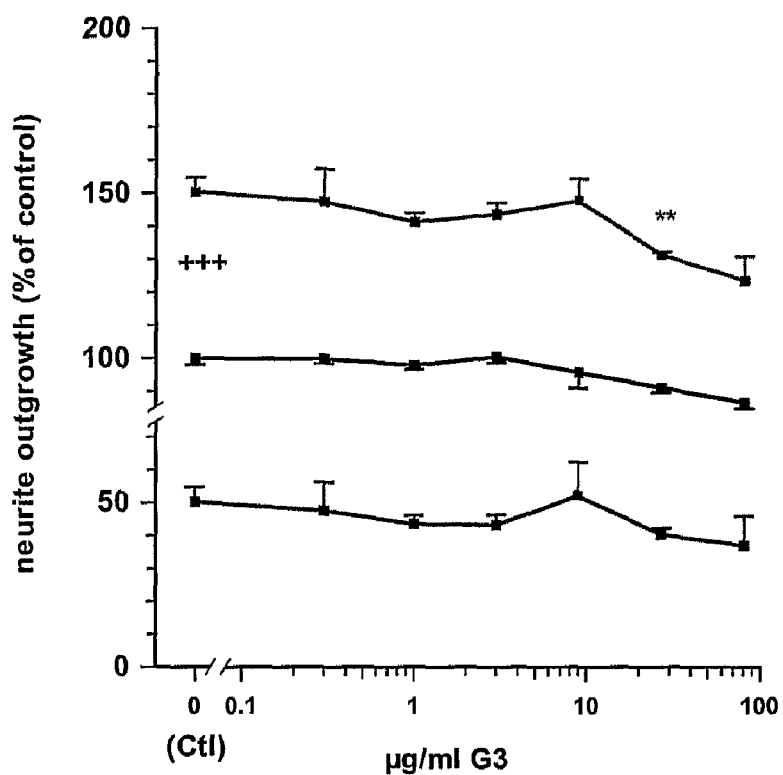
FIG. 8: G3 interferes with NCAM-induced neurite outgrowth in hippocampal neurons grown in co-culture with control fibroblasts or NCAM-expressing fibroblasts. Neurons were grown on top of either control fibroblasts (middle curve) or NCAM-expressing fibroblasts (upper curve) and stimulated with G3 (0.3, 1, 3, 9, 27 and 81 μg/ml) for 24 hours. Neurons grown in medium alone (lower curve) served as controls. Results are expressed as percentage of control (non-stimulated neurons on control fibroblasts) and presented as means±S.E.M. For controls on control fibroblasts absolute length of neurite outgrowth 34.20 μm±0.68 μm. The figure is based on results from 4 independent experiments. The mean neurite outgrowth lengths were compared using separate one-way ANOVAs for repeated measurements. $F_{(4, 15)}=2.440$, $p=0.1039$, shows that there is no overall significant effect of GDNFp3-treatment for neurons grown on control fibroblasts. $F_{(4, 15)}=5.967$, $p<0.01$ shows that there is an overall statistical significant effect of G3-treatment for neurons grown on NCAM-expressing fibroblasts. This effect seems to be inhibitory at higher concentrations of G3. The effect of individual concentrations of G3 was compared to the matching control using post-testing with Tukeys multiple comparisons test. * beside upper curve indicates p-values for comparison to non-stimulated cells grown on NCAM-expressing fibroblasts. The two controls were compared using a paired t-test, which showed that they are statistically significant different (p-value indicated by + beside middle curve). For each concentration the difference between neurite outgrowth in neurons grown on control fibroblasts and in neurons grown on NCAM-expressing fibroblasts was calculated and expressed as percentage of control (non-stimulated neurons on control fibroblasts) (blue curve). One-way ANOVA for repeated measurements showed that the mean differences are not all the same $(F_{(4, 15)}=1.314, p=0.3199)$. The difference at individual concentrations of GDNFp2 was compared to the difference of the two controls using post-testing with Tukeys multiple comparisons test. * beside lower curve indicates p-values.
Figure 9:
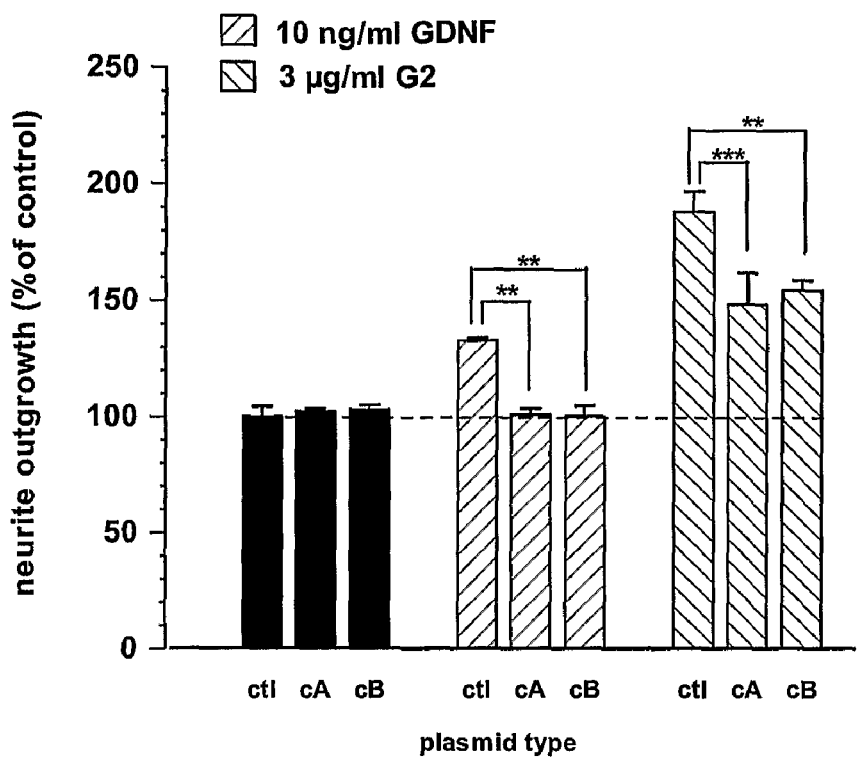
FIG. 9: NCAM-involvement in neurite outgrowth mediated by GDNF or G2. Hippocampal neurons transfected with cyt-NCAM-A, cyt-NCAM-B or empty vector were grown on control fibroblasts and stimulated with 10 ng/ml GDNF or 3 μg/ml GDNFp1 for 18 hours. Medium alone was added to controls.  $p<0.01$, * $p<0.001$.
Figure 10:
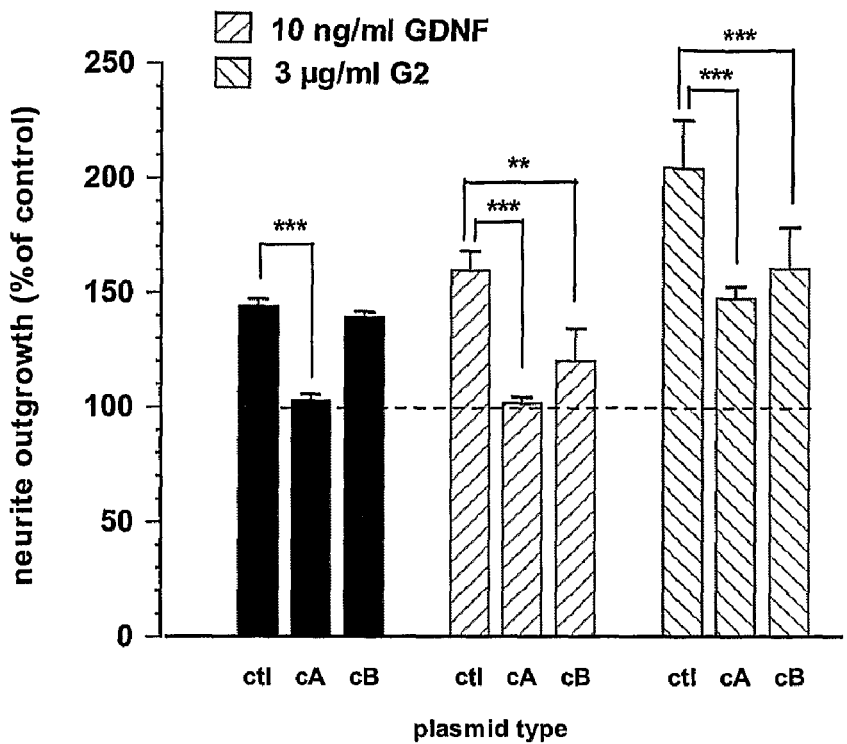
FIG. 10: NCAM-involvement in neurite outgrowth mediated by GDNF or G2. Hippocampal neurons transfected with cyt-NCAM-A, cyt-NCAM-B or empty vector were grown on NCAM-expressing fibroblasts and stimulated with 10 ng/ml GDNF or 3 μg/ml GDNFp1 for 18 hours. Medium alone was added to controls.  $p<0.01$, * $p<0.001$.
Figure 11:
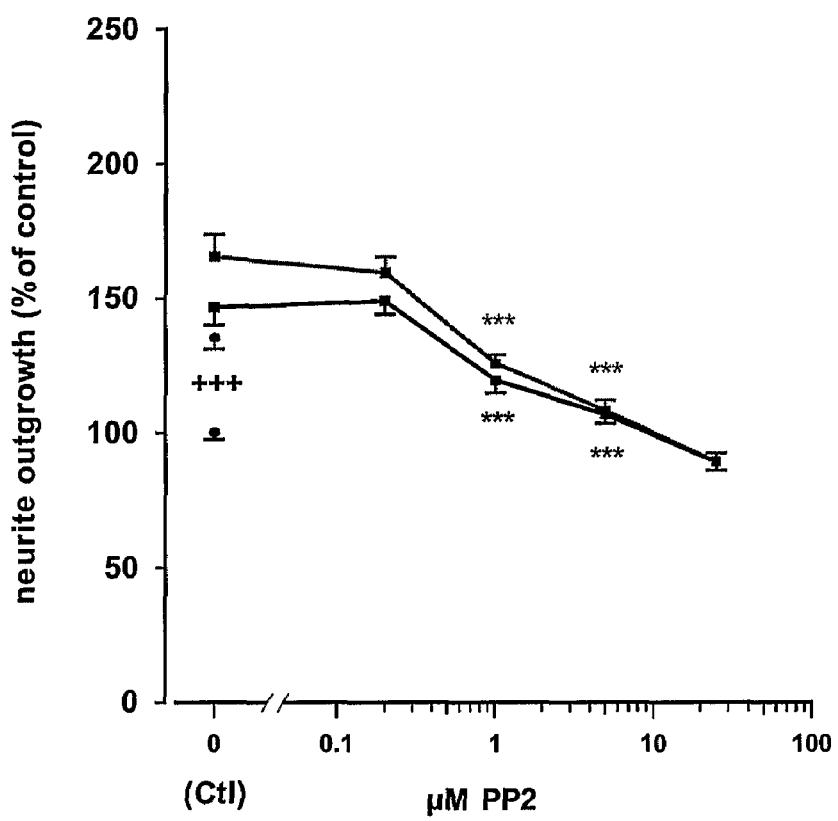
FIG. 11: The Fyn-kinase inhibitor PP2 decreases GDNF-induced neurite outgrowth in hippocampal neurons. Neurons were grown on top of either control fibroblasts (lower (as of lowest concentration) curve) or NCAM-expressing fibroblasts (upper (as of lowest concentration) curve). 10 ng/ml GDNF was used for stimulation, and neurons were incubated with PP2 (0.2, 1, 5, and 25 μM for 24 hours. Neurons stimulated with GDNF, but without PP2 served as positive controls. Neurons grown in medium alone served as negative controls, and are indicated by the circles not connected to the curves. Results are expressed as percentage of negative control (non-stimulated neurons on control fibroblasts) and presented as means±S.E.M. The figure is based on results from 6 independent experiments. The mean neurite lengths were compared using separate one-way ANOVAs. *** and +++$p<0.001$ when compared to the corresponding controls.
Figure 12:
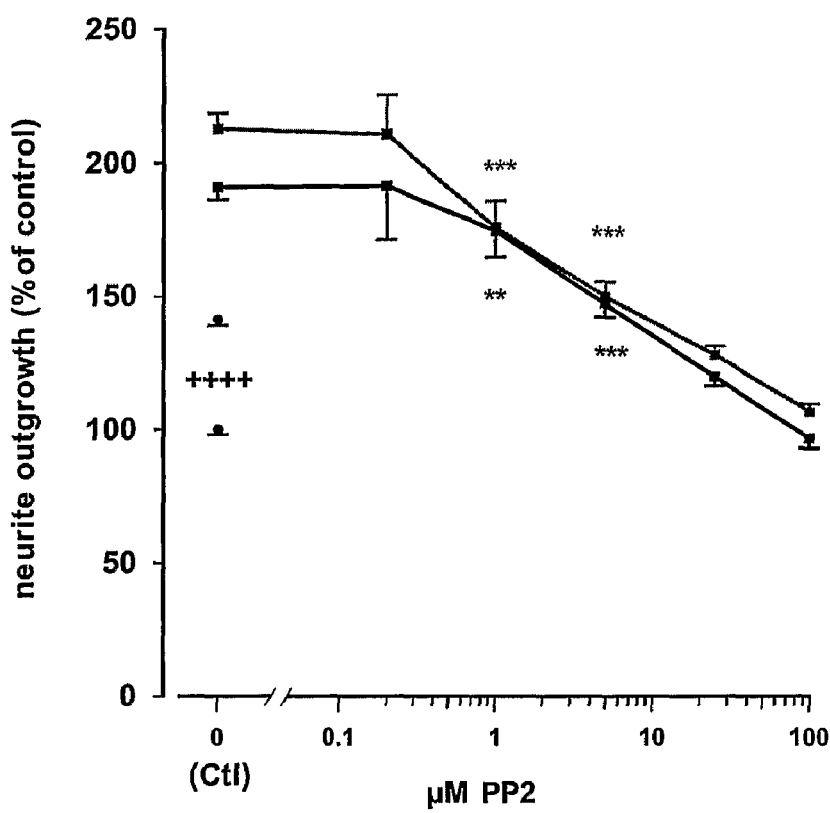
FIG. 12: The Fyn-kinase inhibitor PP2 decreases G2-induced neurite outgrowth in hippocampal neurons. Neurons were grown on top of either control fibroblasts (lower (as of lowest concentration) curve) or NCAM-expressing fibroblasts (upper (as of lowest concentration) curve). 3 μg/ml G2 was used for stimulation, and neurons were incubated with PP2 (0.2, 1, 5, 25, and 100 μM for) for 24 hours. Neurons stimulated with G2, but without PP2 served as positive controls. Neurons grown in medium alone served as negative controls, and are indicated by the circles not connected to the curves. Results are expressed as percentage of negative control (non-stimulated neurons on control fibroblasts) and presented as means±S.E.M. The figure is based on results from 6 independent experiments. The mean neurite lengths were compared using separate one-way ANOVAs. *** and +++$p<0.001$ or ++++$p<0.0001$ when compared to the corresponding controls.
Figure 13:
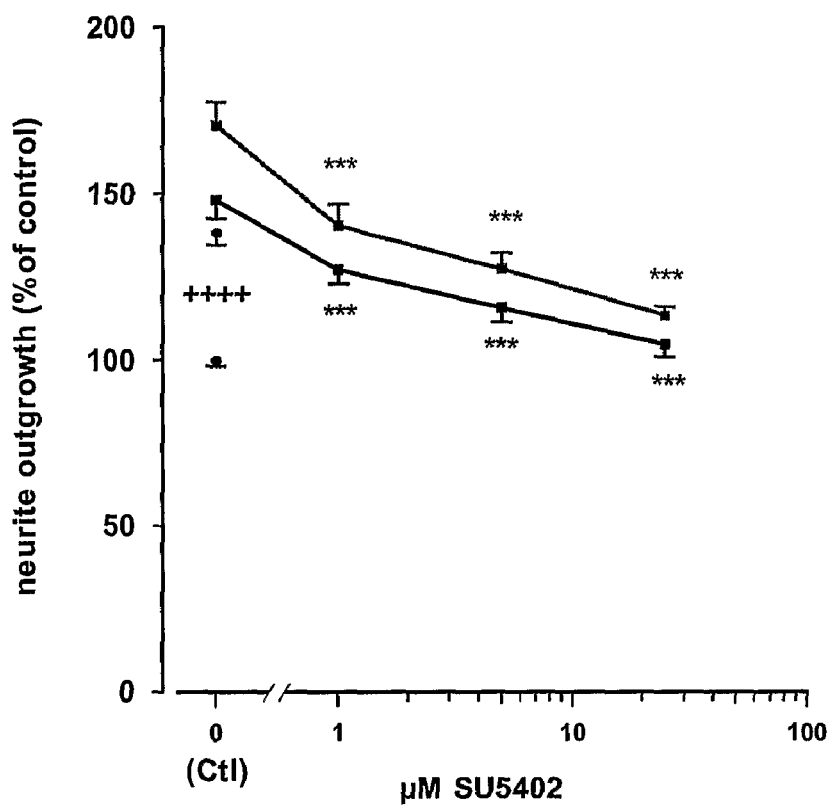
FIG. 13: The FGFR-inhibitor SU5402 decreases GDNF-induced neurite outgrowth in hippocampal neurons. Neurons were grown on top of either control fibroblasts (lower curve) or NCAM-expressing fibroblasts (upper curve). 10 ng/ml GDNF was used for stimulation, and neurons were incubated with SU5402 (1, 5, and 25 μM. Neurons stimulated with GDNF, but without SU5402 served as positive controls. Neurons grown in medium alone served as negative controls, and are indicated by the black and red circles not connected to the curves. Results are expressed as percentage of negative control (non-stimulated neurons on control fibroblasts) and presented as means±S.E.M. The mean neurite outgrowth lengths were compared using one-way ANOVAs. * beside lower curve indicates p-values for comparison to the positive control grown on control fibroblasts, whereas * beside upper curve indicates p-values for comparison to the positive control grown on NCAM-expressing fibroblasts. The two negative controls were compared using a paired t-test, which showed that they are statistically significantly different (p-value indicated by + beside middle curve).
Figure 14:
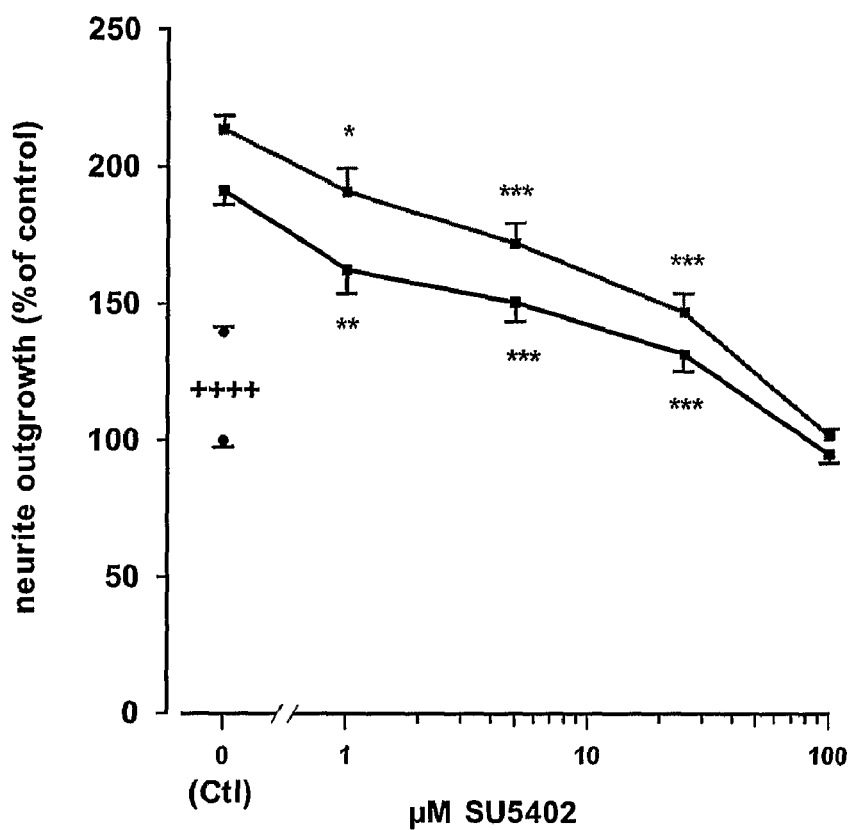
FIG. 14: The FGFR-inhibitor SU5402 decreases G2-induced neurite outgrowth in hippocampal neurons. Neurons were grown on top of either control fibroblasts (lower curve) or NCAM-expressing fibroblasts (upper curve). 3 μg/ml GDNFp1 was used for stimulation, and neurons were incubated with SU5402 (1, 5, 25, and 100 μM for) for 24 hours. Neurons stimulated with G2, but without SU5402 served as positive controls. Neurons grown in medium alone served as negative controls, and are indicated by the circles not connected to the curves. Results are expressed as percentage of negative control (non-stimulated neurons on control fibroblasts) and presented as means±S.E.M. The mean neurite outgrowth lengths were compared using one-way ANOVA. The effect of individual concentrations of SU5402 was compared to the matching positive control using post-testing with Tukeys multiple comparisons test. * beside lower curve indicates p-values for comparison to the positive control grown on control fibroblasts, whereas * beside upper curve indicates p-values for comparison to the positive control grown on NCAM-expressing fibroblasts. The two negative controls were compared using a paired t-test, which showed that they are statistically significantly different (p-value indicated by + beside middle curve).
Figure 15:
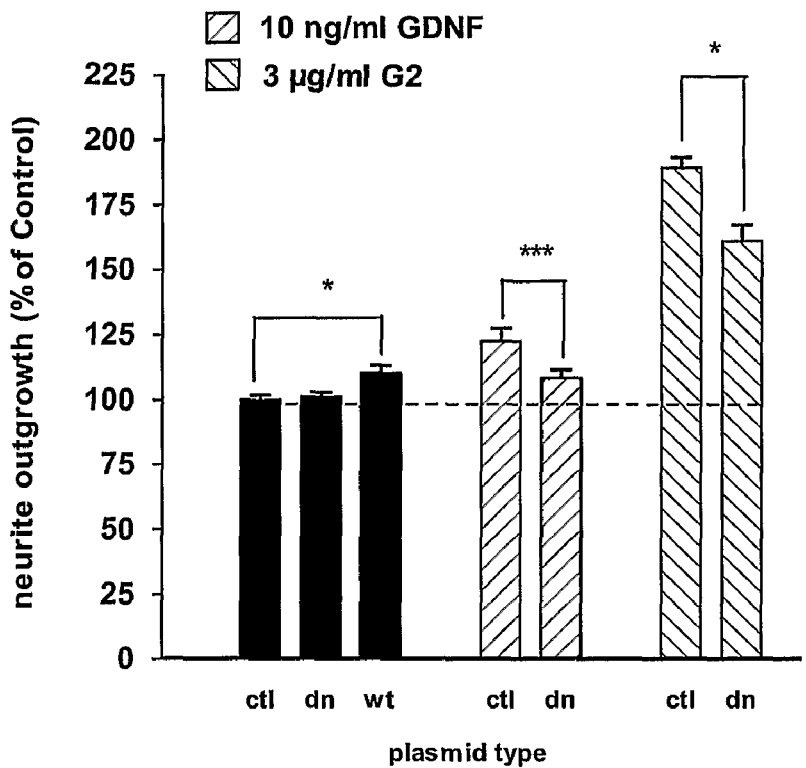
FIG. 15: Transfection with dominant negative FGFR decreases neurite outgrowth mediated by GDNF or G2. Hippocampal neurons transfected with dnFGFR, wtFGFR or empty vector were grown on control fibroblasts and stimulated with 10 ng/ml GDNF or 3 μg/ml GDNFp1 for 18 hours. Medium alone was added to controls. The figure is based on results from 5 independent experiments. Statistical evaluation was done by applying paired t-test. * $p<0.05$ and *** $p<0.001$, when compared to the corresponding controls.
Figure 16:
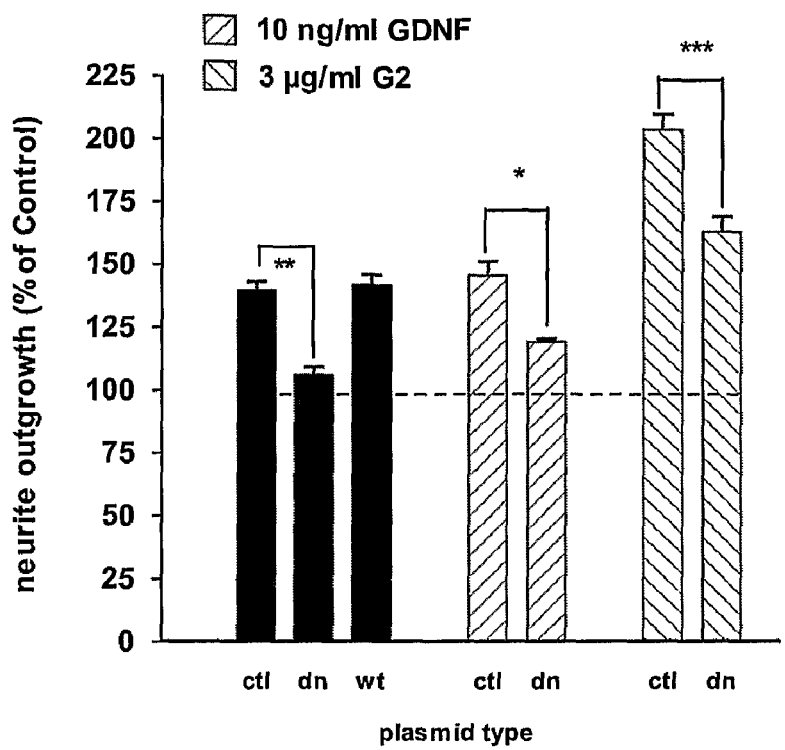
FIG. 16: Transfection with dominant negative FGFR decreases neurite outgrowth mediated by GDNF or G2. Hippocampal neurons transfected with dnFGFR, wtFGFR or empty vector was grown on NCAM-expressing fibroblasts and stimulated with 10 ng/ml GDNF or 3 μg/ml GDNFp1 for 18 hours. Medium alone was added to controls. The figure is based on results from 5 independent experiments. Statistical evaluation was done by applying paired t-test. * p<0.05, **p<0.01 and p<0.001, when compared to the corresponding controls.
Figure 17:
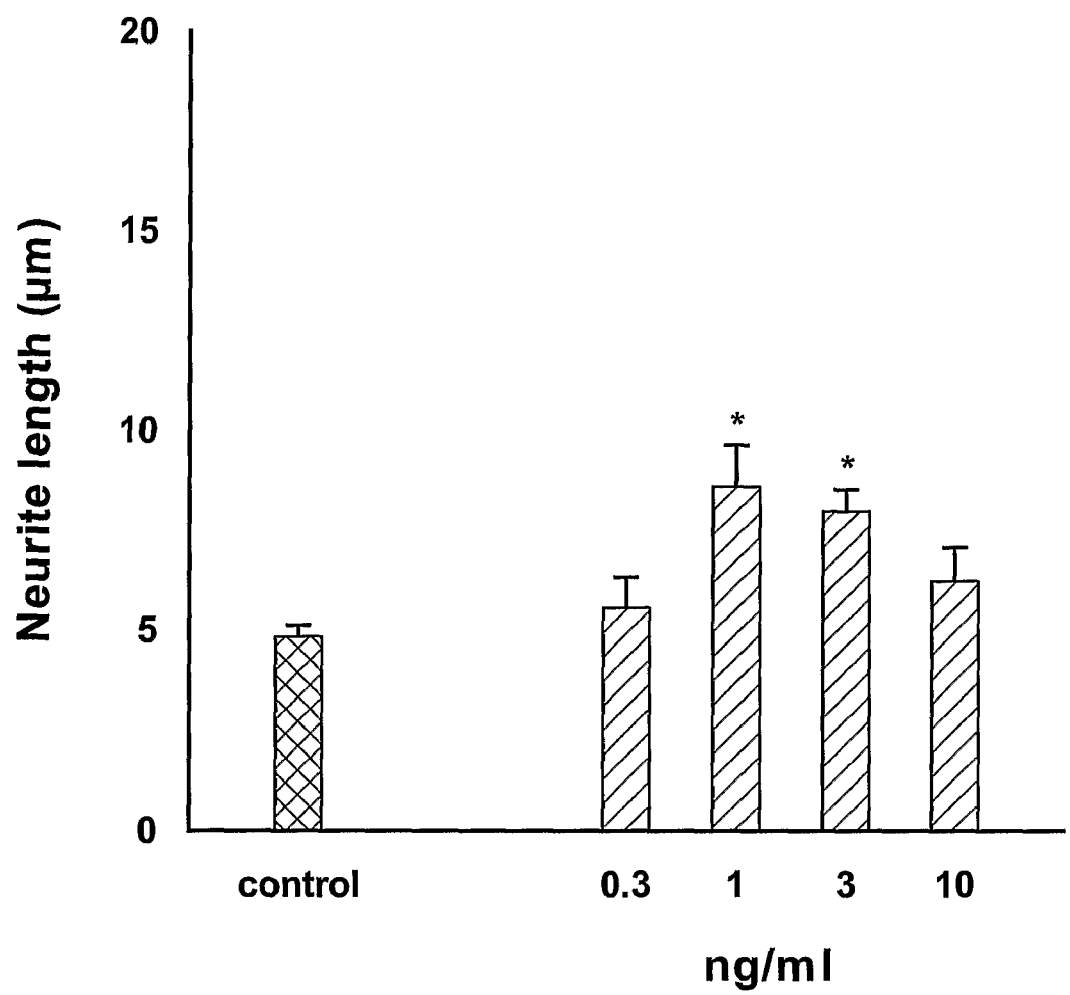
FIG. 17. Effect of artemin on neurite outgrowth from cerebellar granule neurons (CGN). * p<0.05, when compared to the untreated control.
Figure 18:
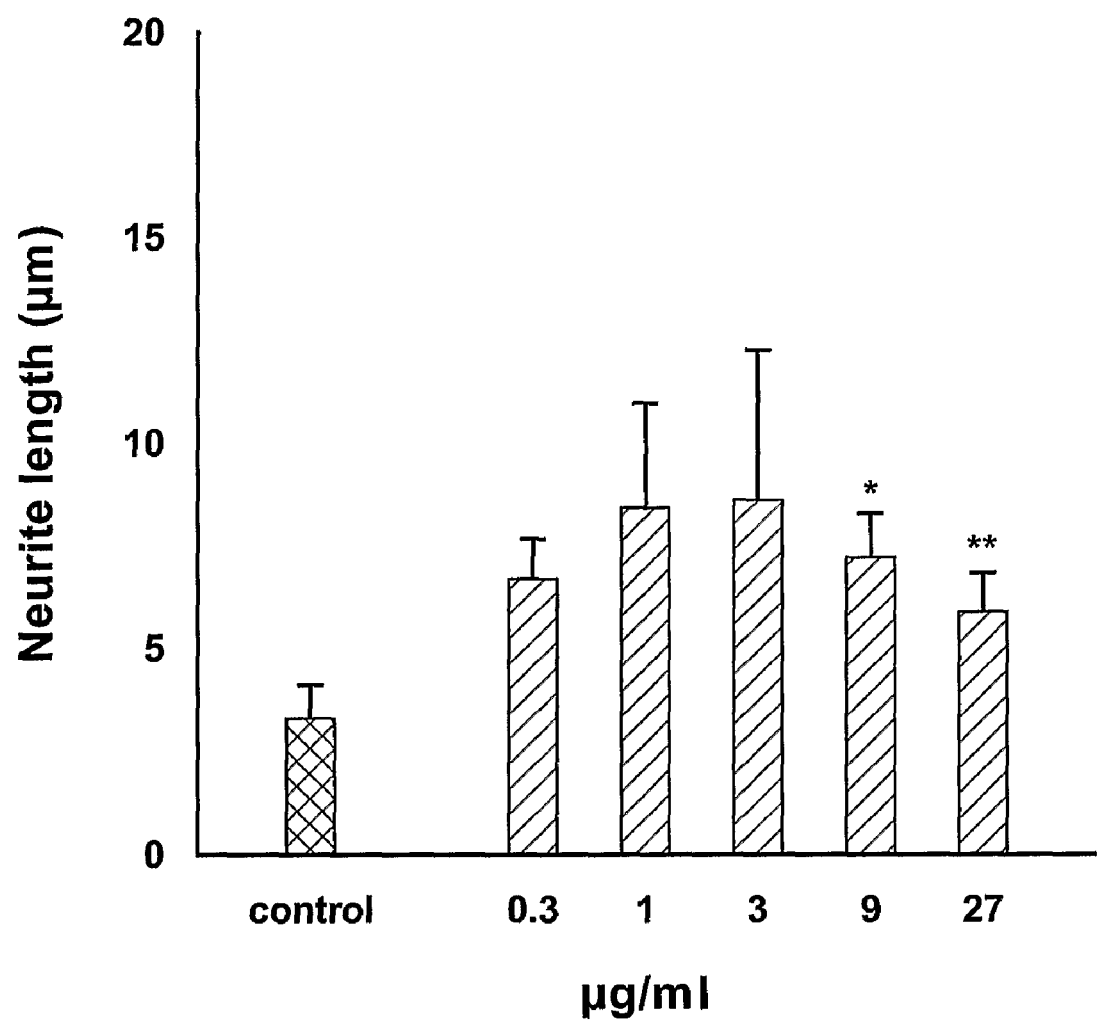
FIG. 18. Effect of the A1 peptide on neurite outgrowth from CGN. * p<0.05 and ** p<0.01, when compared to the untreated control.
Figure 19:
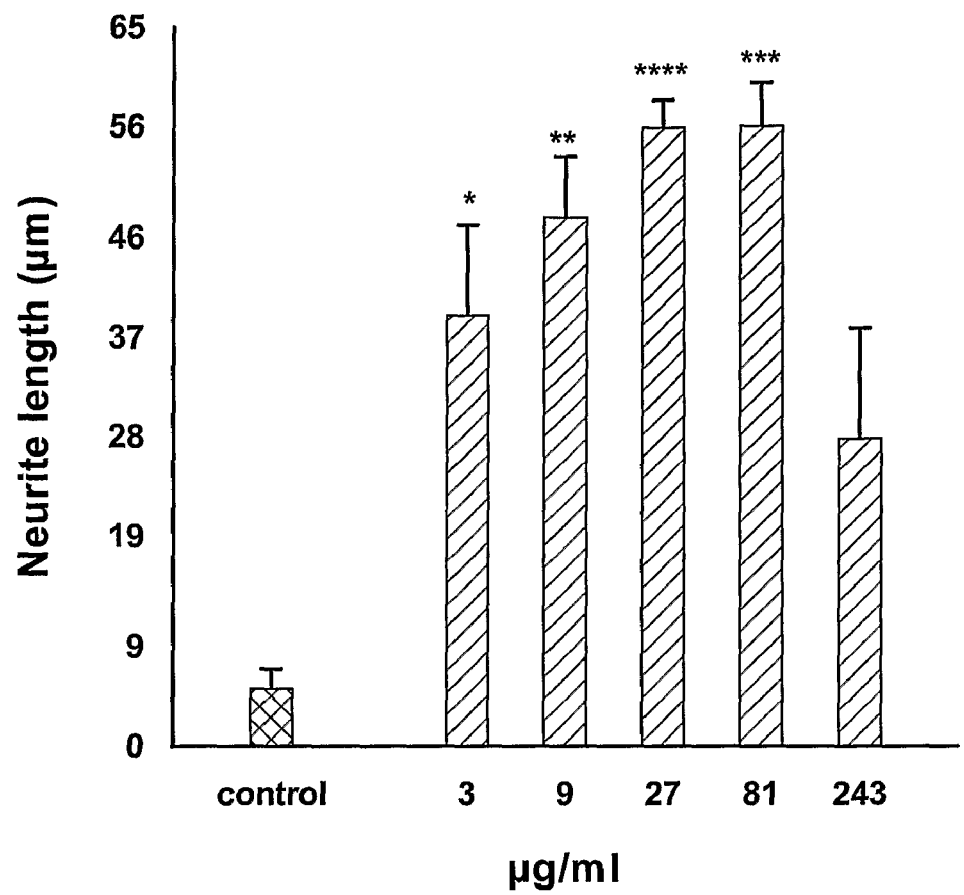
FIG. 19. Effect of the A2 peptide on neurite outgrowth from CGN. * p<0.05,  p<0.01, * p<0.001, and **** p<0.0001, when compared to the untreated control.
Figure 20:
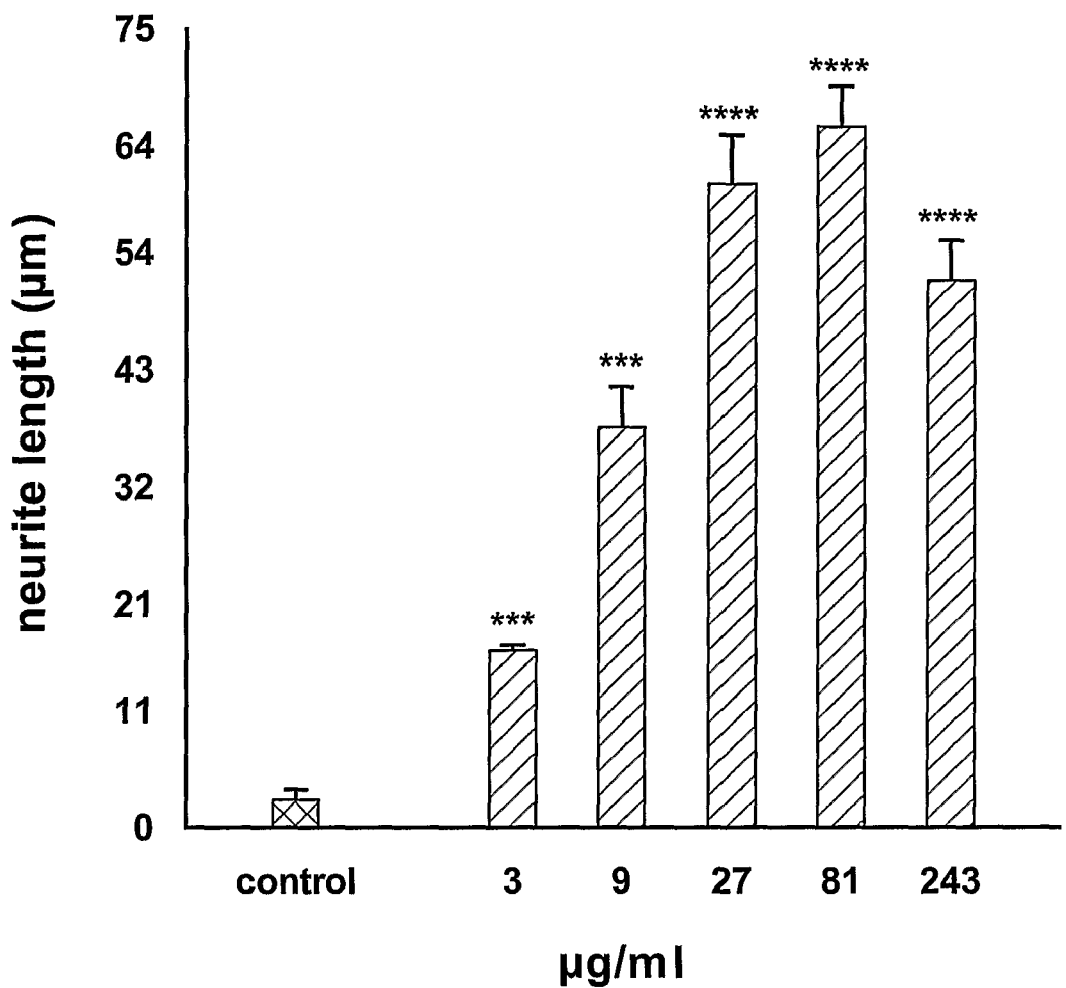
FIG. 20 Effect of the A3 peptide on neurite outgrowth from CGN. * p<0.001, and ** p<0.0001, when compared to the untreated control.
Figure 21:
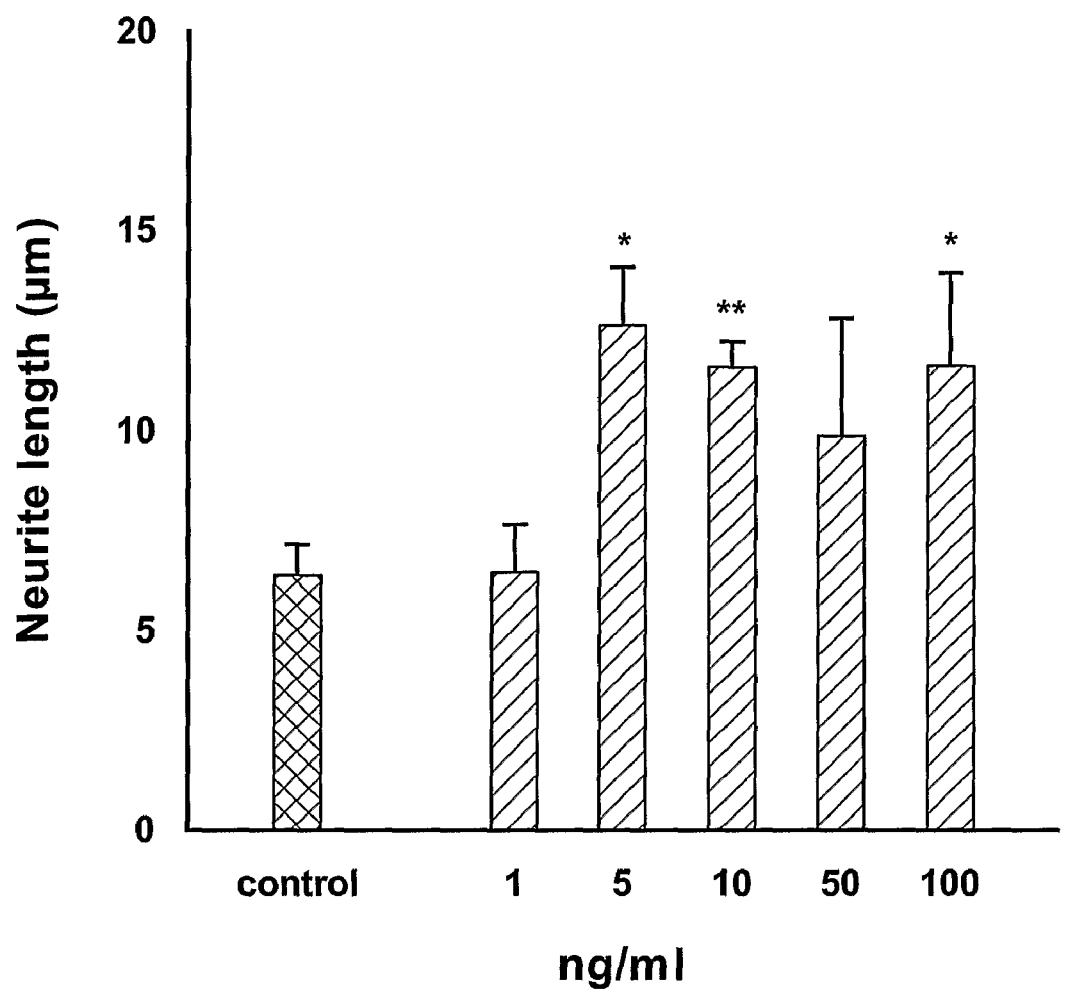
FIG. 21. Effect of neurturin on neurite outgrowth from CGN. * p<0.05 and ** p<0.01, when compared to the untreated control.
Figure 22:
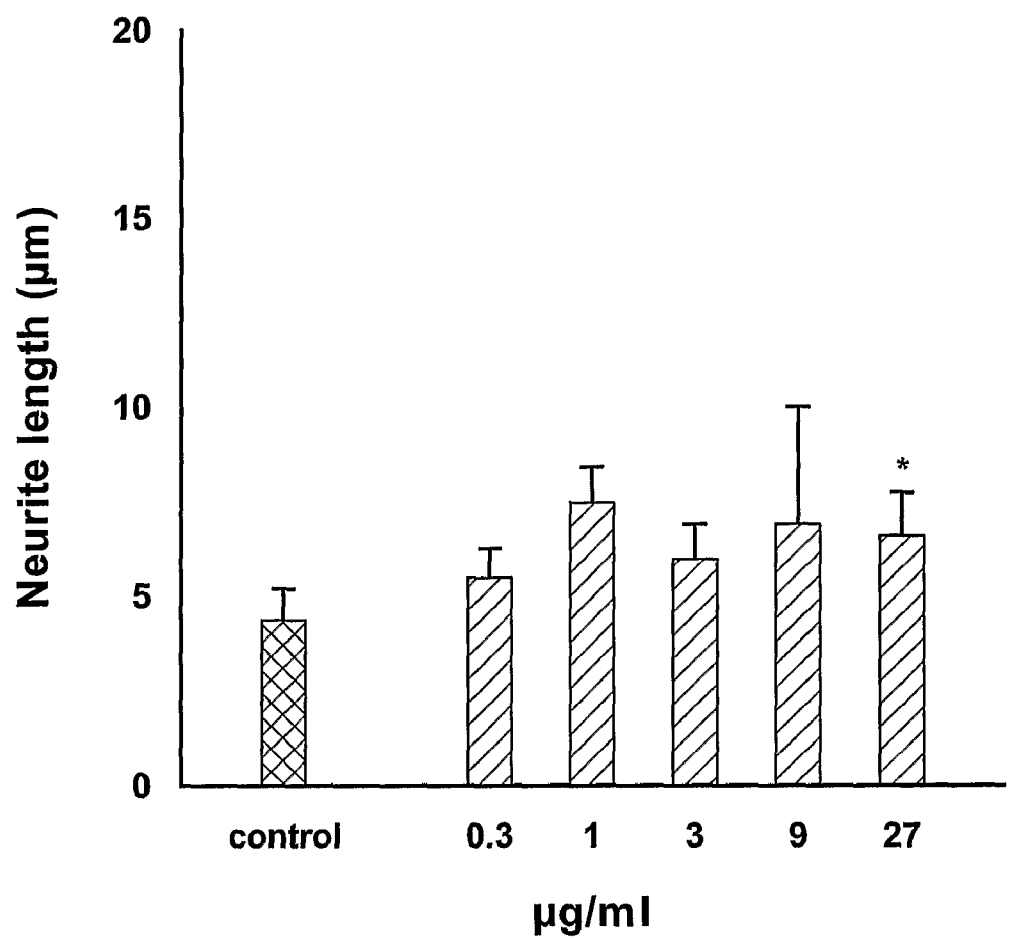
FIG. 22. Effect of the N1 peptide on neurite outgrowth from CGN. * p<0.05, when compared to the untreated control.
Figure 23:
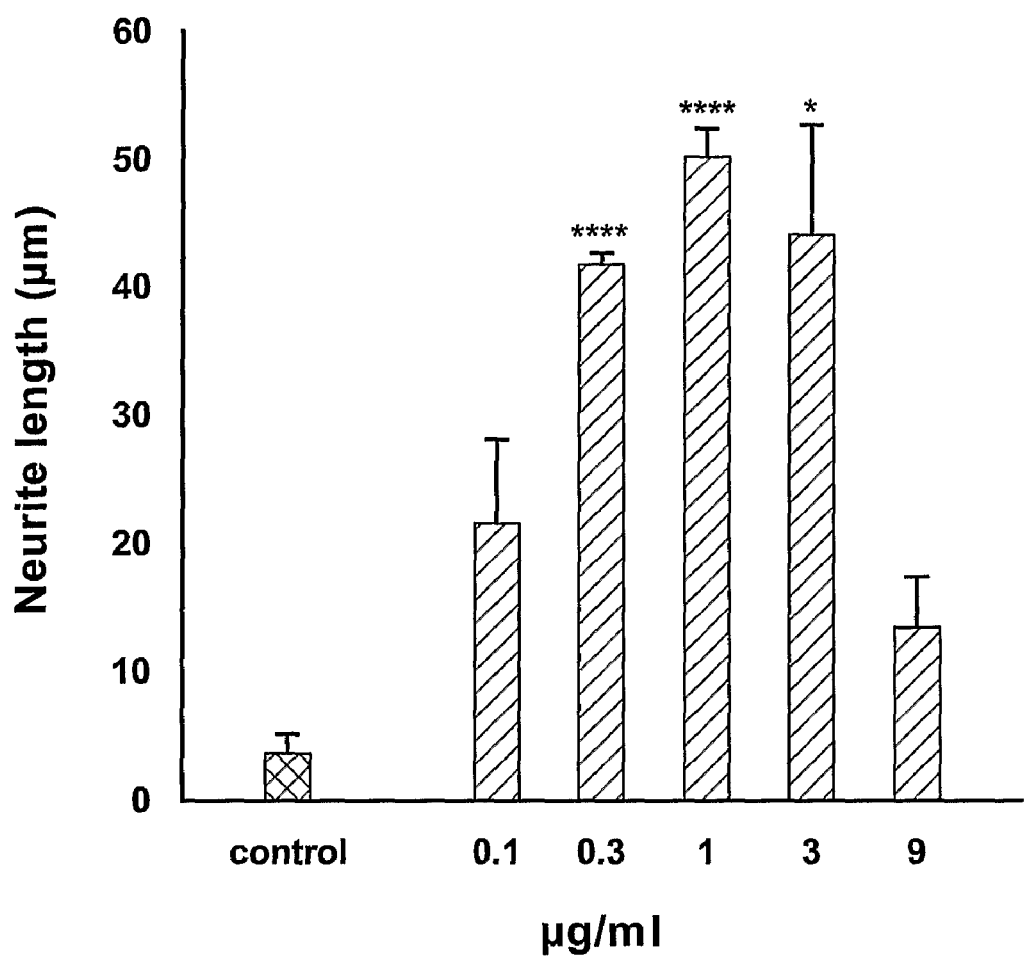
FIG. 23. Effect of the N2 peptide on neurite outgrowth from CGN. * p<0.05 and p<0.0001, when compared to the untreated control.
Figure 24:
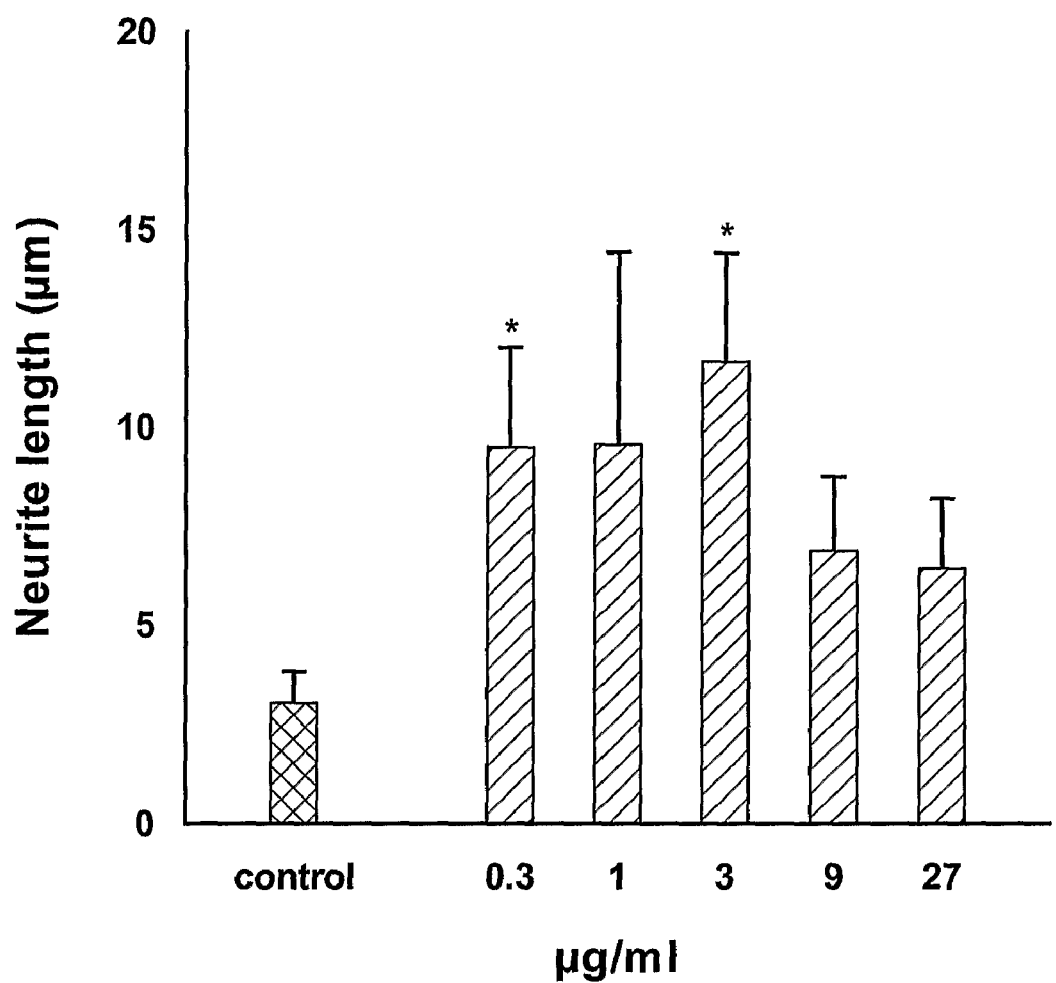
FIG. 24. Effect of the N3 peptide on neurite outgrowth from CGN. * p<0.05, when compared to the untreated control.
Figure 25:
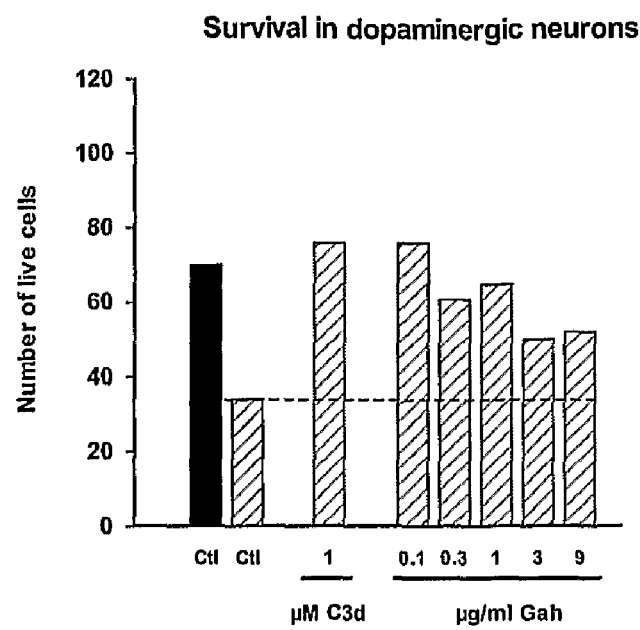
FIG. 25. Effect of a GDNF-derived peptide, Gah (SEQ ID NO: 9; ETTYDKILKNLSRNR), on survival of dopaminergic neurons. Diagram indicates that Gah increases the survival of dopaminergic neurons.
Figure 26:
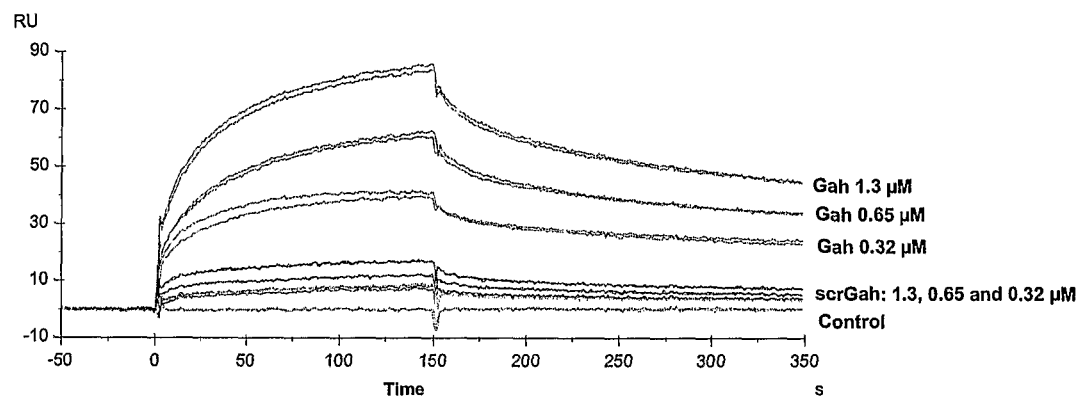

FIG. 26. Binding analysis by surface plasmon resonance (SPR). Binding of a GDNF-derived peptide, Gah (SEQ ID NO: 9 ETTYDKILKNLSRNR), to the Ig1-2 modules of NCAM. Results indicate that the Gah peptide is probably part of the GDNF binding site for the neural cell adhesion molecule (NCAM).

Figure 27:
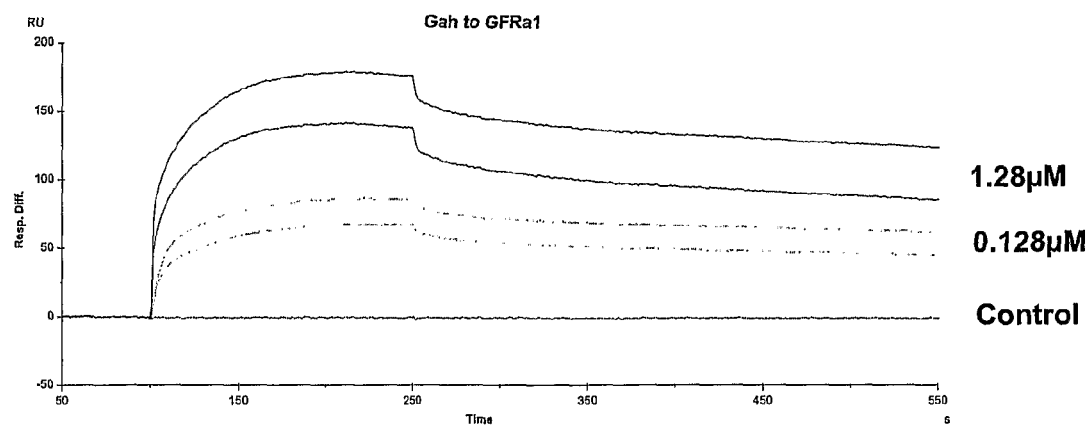

FIG. 27. Binding analysis by surface plasmon resonance (SPR). SPR shows binding of a GDNF-derived peptide, Gah (SEQ ID NO: 9, ETTYDKILKNLSRNR), to the GFRα1 receptor.

Figure 28:
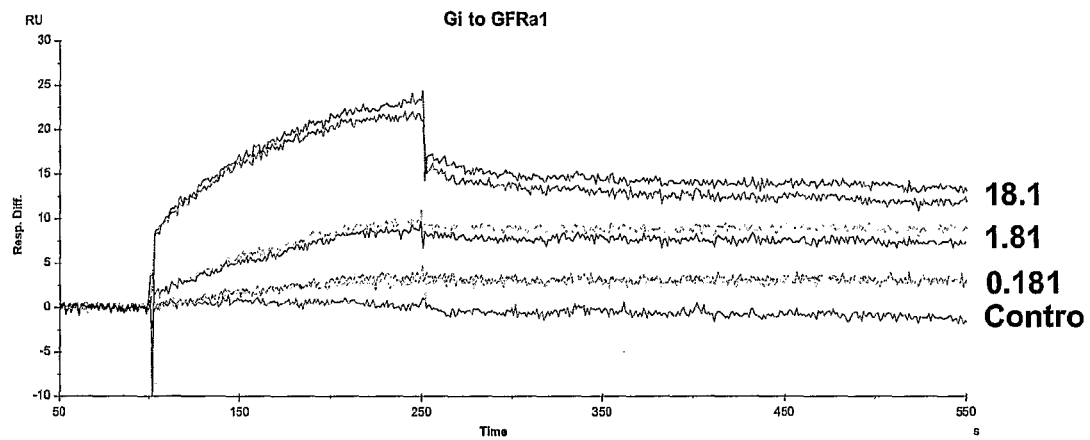

FIG. 28. Binding analysis by surface plasmon resonance (SPR). The figure shows binding of the GDNF-derived peptide, G1 (SEQ ID NO: 16, DDLSFLDDNLVY), to the GFRα1 receptor.

Figure 29:
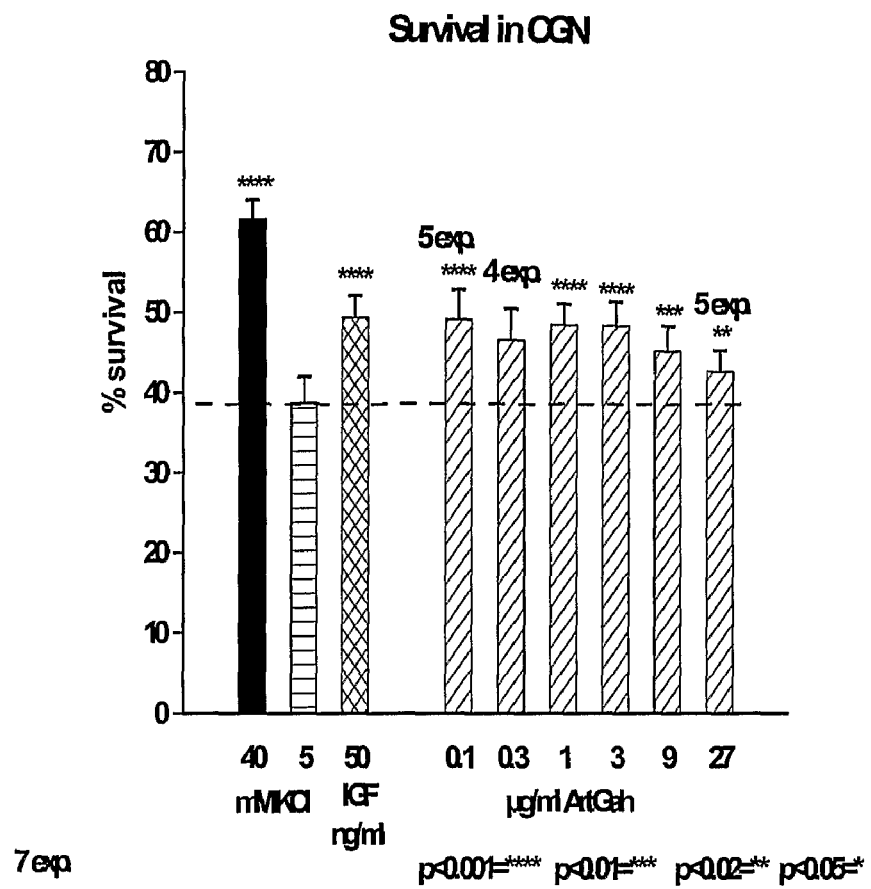

FIG. 29. Effect of an artemin-derived peptide, ArtGah (SEQ ID NO: 10, RSPHDLSLASLLGAG), on survival of cerebellar granule neurons (CGN). Diagram indicates that ArtGah increases the survival of CGNs.

Figure 30:
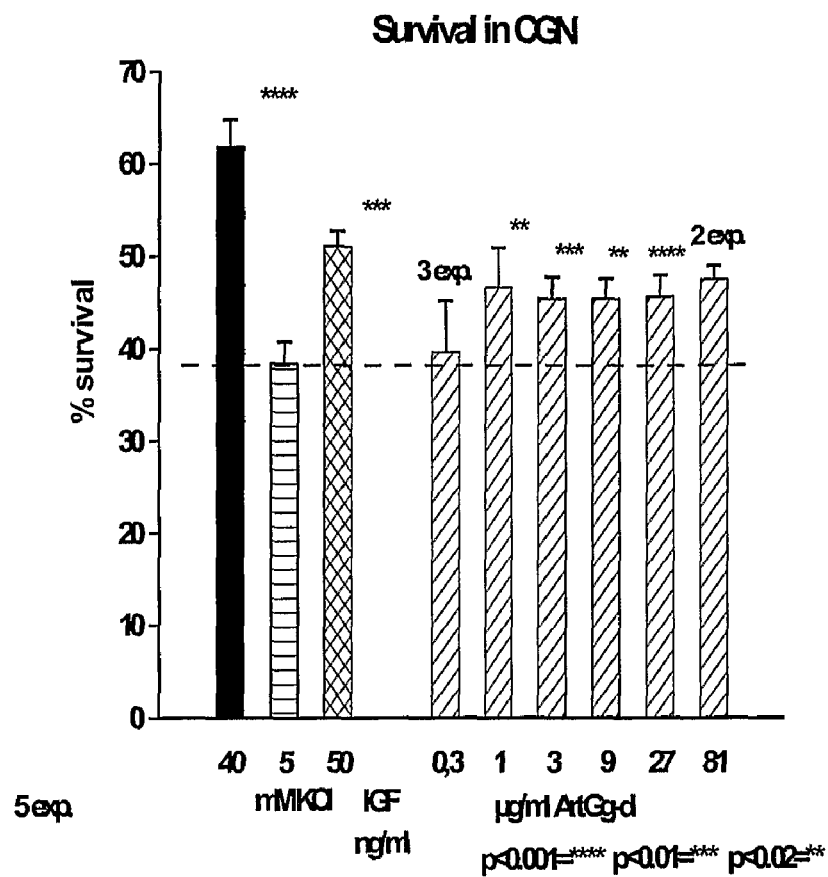

FIG. 30. Effect of an artemin-derived peptide, ArtGg (SEQ ID NO: 2, VPVRALGLGHRSDEL), on survival of cerebellar granule neurons (CGN). Diagram shows that ArtGg increases the survival of CGNs.

Figure 31:
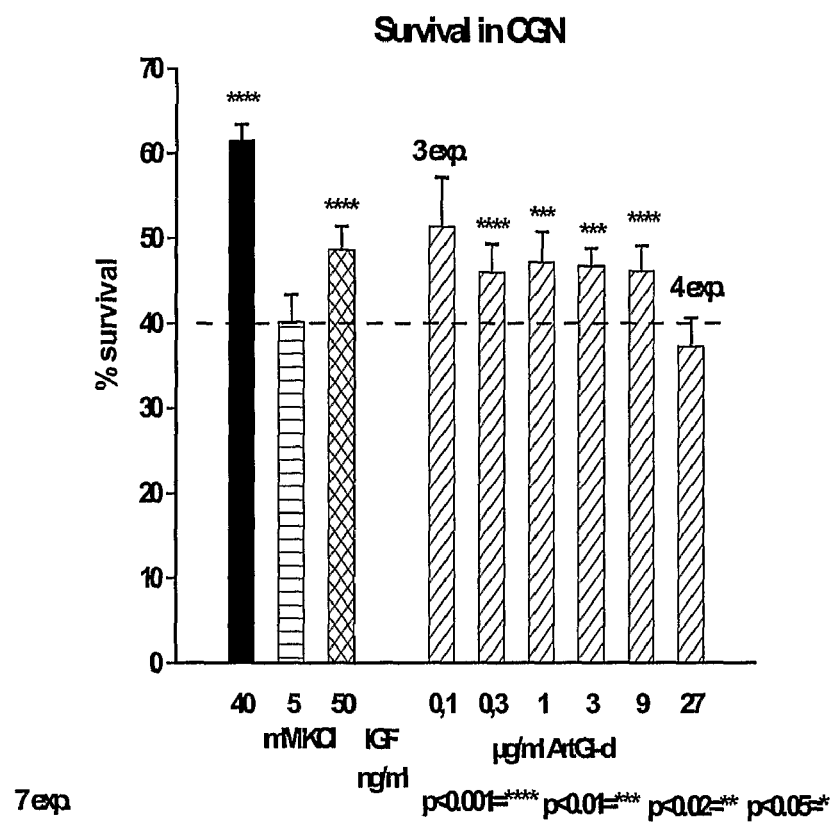

FIG. 31. Effect of an artemin-derived peptide, ArtGi (SEQ ID NO: 17, EAVSFMDVNSTWR), on survival of cerebellar granule neurons (CGN). Diagram shows that ArtGi increases the survival of CGNs.

Figure 32:
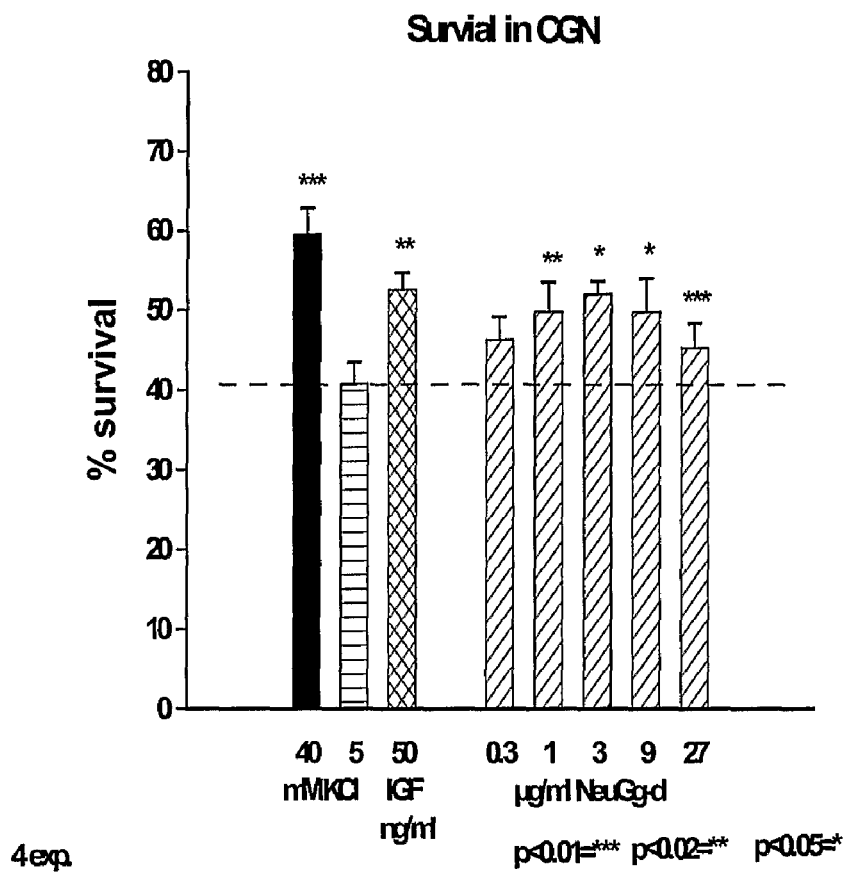

FIG. 32. Effect of a neurturin-derived peptide, NeuGg (SEQ ID NO: 3, VRVSELGLGYASDET), on survival of cerebellar granule neurons (CGN). Diagram shows that NeuGg increases the survival of CGNs.

Figure 33:
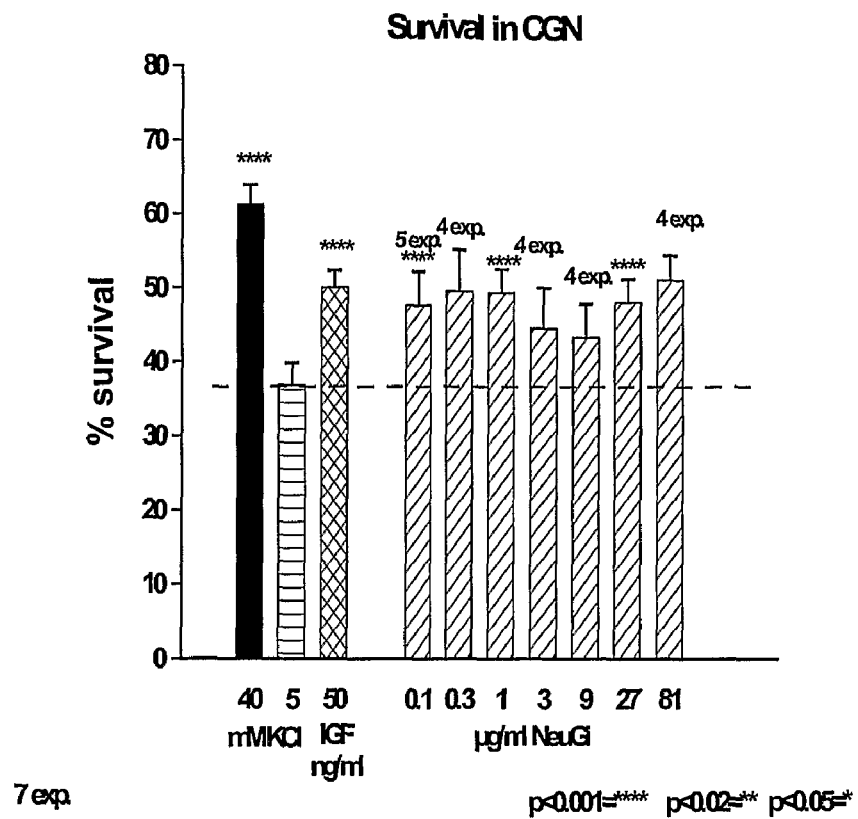

FIG. 33. Effect of a neurturin-derived peptide, NeuGi (SEQ ID NO: 18, DEVSFLDAHSRY), on survival of cerebellar granule neurons (CGN). Diagram shows that NeuGi increases the survival of CGNs.

Figure 34:
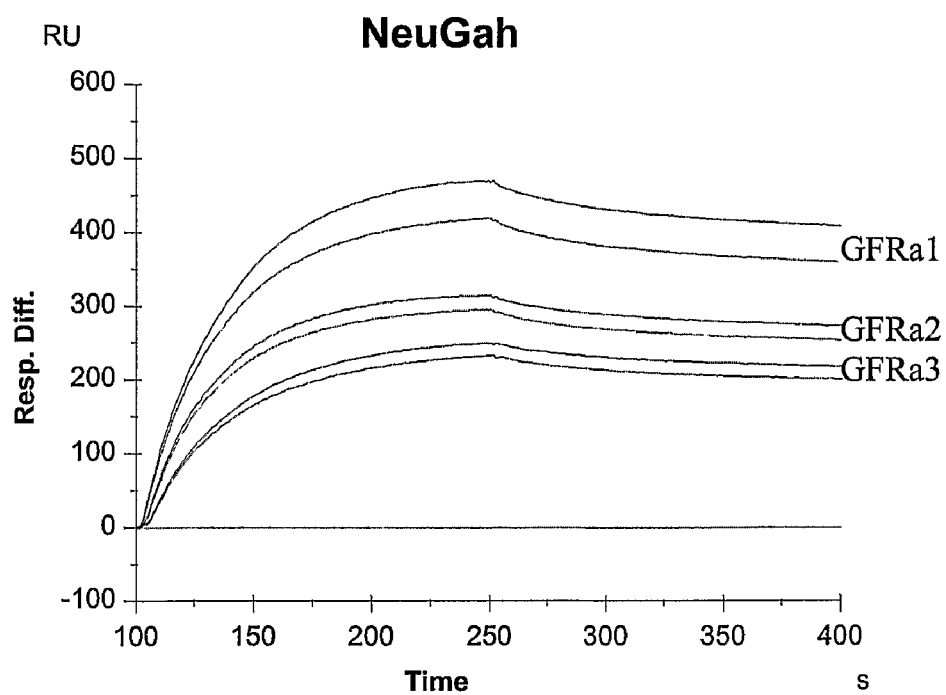

FIG. 34. Binding analysis by surface plasmon resonance (SPR). The figure shows binding of a neurturin-derived peptide, NeuGah (SEQ ID NO: 11, ARVYDLGLRRLRQRR), to the GFRα receptors.

Figure 35:
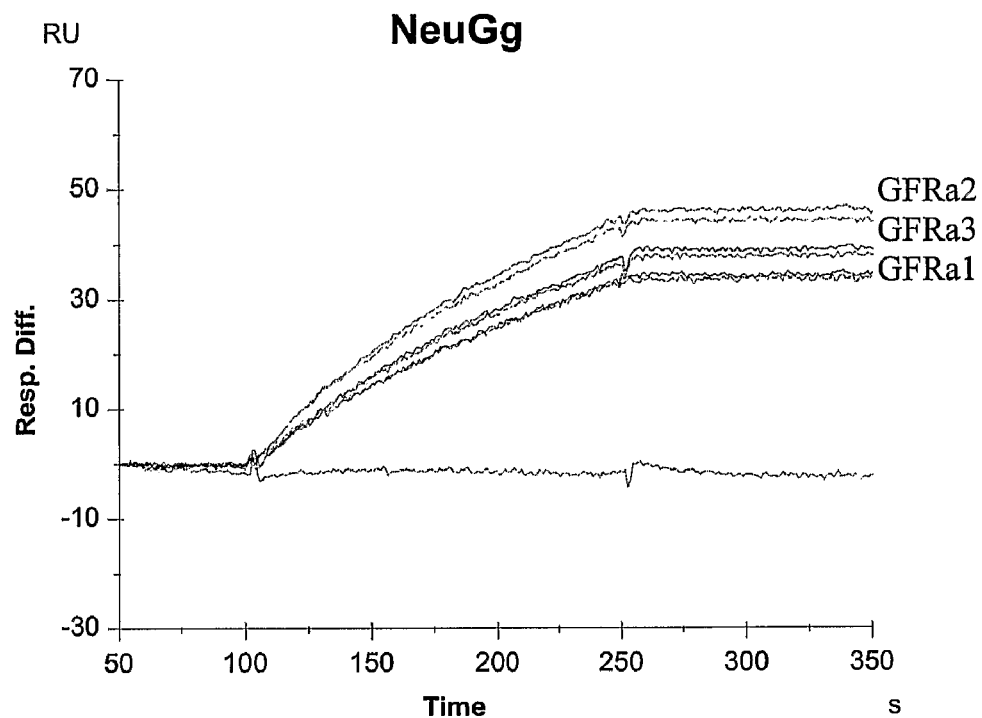

FIG. 35. Binding analysis by surface plasmon resonance (SPR). The figure shows binding of a neurturin-derived peptide, NeuGg (SEQ ID NO: 3, VRVSELGLGYASDET), to the GFRα receptors.

Figure 36:
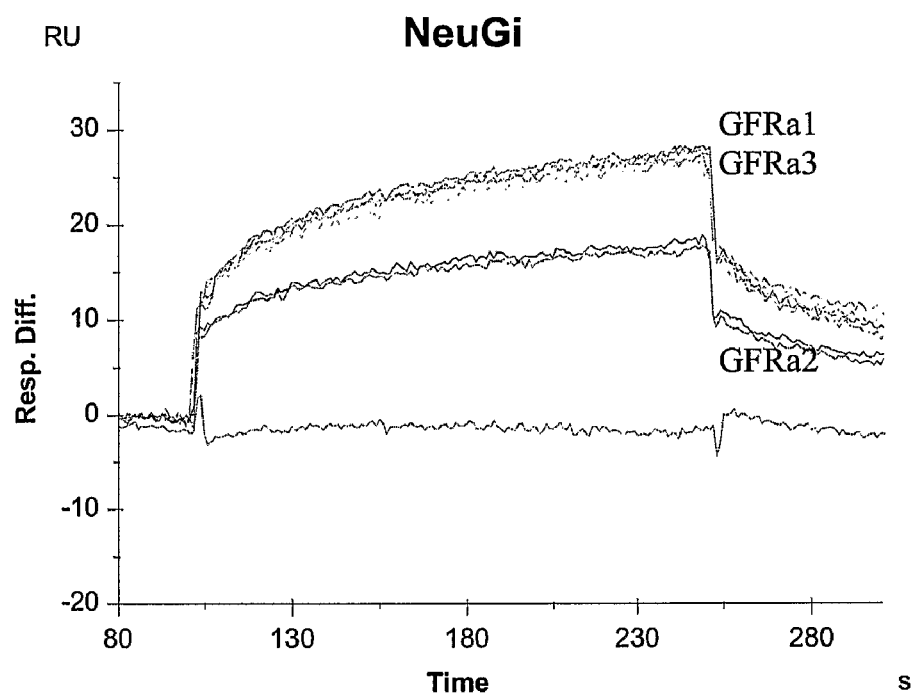

FIG. 36. Binding analysis by surface plasmon resonance (SPR). The figure shows binding of a neurturin-derived peptide, NeuGi (SEQ ID NO: 18, DEVSFLDAHSRY), to the GFRα receptors.

Figure 37:
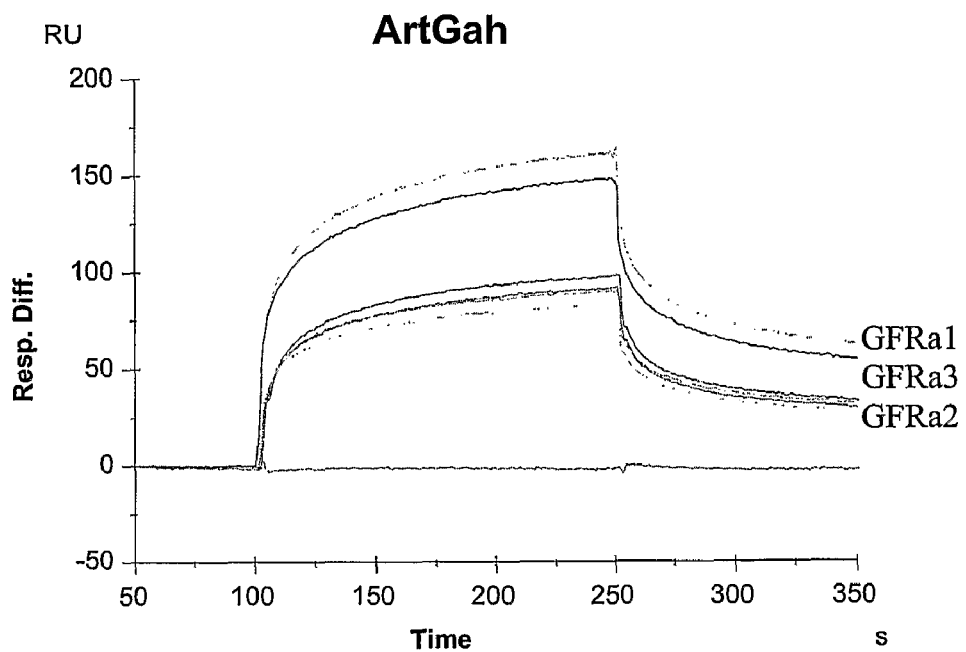

FIG. 37. Binding analysis by surface plasmon resonance (SPR). The figure shows binding of an artemin-derived peptide, ArtGah (SEQ ID NO: 10, RSPHDLSLASLLGAG), to the GFRα receptors.

Figure 38:
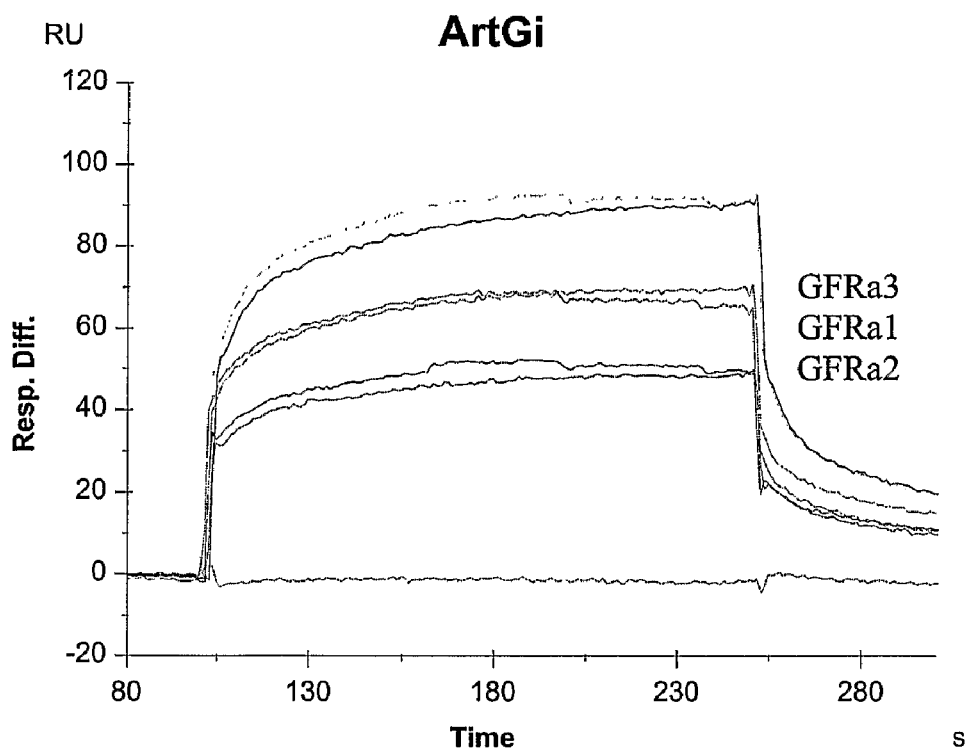

FIG. 38. Binding analysis by surface plasmon resonance (SPR). The figure shows binding of an artemin-derived peptide, ArtGi (EAVSFMDVNSTWR), to the GFRα receptors.

DETAILED DESCRIPTION OF THE INVENTION

Peptide Sequences

First aspect the invention relates to a peptide having a sequence of 6 to 22 contiguous amino acid residues comprising the motif:

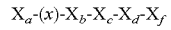

wherein
$X_a$ is amino acid residue D, E, A or G,
(x) is a sequence of 2-3 amino acid residues or a single amino acid residue selected from the group consisting of amino acid residues A, D, E, G, I, K, L, P, Q, S, T and V,
$X_b$ is amino acid residue Y or H, or a hydrophobic amino acid residue, and
at least one of $X_c$, $X_d$ or $X_f$ is a charged or hydrophobic amino acid residue.

According to the invention, in one preferred embodiment $X_a$ may be an acidic amino acid residue, e.g. E or D. In another preferred embodiment $X_a$ may be A or G.

In some embodiments position (x) of the above motif may preferably be occupied by a sequence of any two amino acid residues, wherein a preferred sequence is a sequence of any two of the following residues L, G, A, S, T, K or 1, wherein sequences: L-G, L-A, L-S, T-Q, T-T or K-I are more preferred.

In other embodiments (x) may be a sequence of any three amino acid residues, preferably the residues selected from L, G, A, S, T, K, I, wherein more preferred is sequence L-X-G, X being any amino acid residue, and the most preferred is sequence L-Q-G.

In still other embodiments (x) may be represented by any single amino acid residue, preferably a charged or hydrophobic amino acid residue. More preferably the amino acid residue may be selected from D, E, A, V or P.

The residue at position $X_b$ of the above motif in one preferred embodiment may be A, L, V or W. In another preferred embodiment $X_b$ may be H. Still in another preferred embodiment $X_b$ may be Y.

According to the invention residues $X_c$, $X_d$ or $X_f$ may be independently any amino acid residue, however it is preferred that at least one of $X_c$, $X_d$ or $X_f$ is selected from a charged or hydrophobic amino acid residue. In particular, a charged or hydrophobic residue is preferred at position $X_f$, wherein among hydrophobic residues residues A, I, V, L or M are most preferred, and among charged are most preferred residues R, E or D.

The invention further relates to a peptide comprising an amino acid sequence of the formula

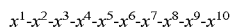

wherein
- $x^1$ is an amino acid residue selected from D, A, E or H,
- $x^2$ is an amino acid residue selected from L, G, T, D, A, E, V or P,
- $x^3$ is an amino acid residue selected from G, Q, I, S, G, L, T, V or A,
- $x^4$ is an amino acid residue selected from L. W, G, A, Y, H, S, F, P or T,
- $x^5$ is an amino acid residue selected from G, K, M, A, R, L, S, F or I,
- $x^6$ is an amino acid residue selected from Y, H, W, K, N, S, R, A, M, L, D or V,
- $x^7$ is an amino acid residue selected from E, R, A, I, V, W, L, D or Y,
- $x^8$ is an amino acid residue selected from T, S, H, L, R, D, V, A or Y,
- $x^9$ is an amino acid residue selected from K, D, E, R, G, Q, A, S, N, H, V or I,
- $x^{10}$ is an amino acid residue selected from E, P, N, A, R, G, L or S, wherein said amino acid sequence is comprising the motif described above.

A peptide comprising the above amino acid sequence is preferably 10 to 22 amino acid residues long, or a fragment thereof comprising least 6 amino acid residues comprising the motif of the invention. According to the invention such amino acid sequence preferably comprises a sequence selected from the following sequences:

| | |
|---|---|
| LNVTDLGLGYETKEE | (SEQ ID NO: 1) |
| VPVRALGLGHRSDEL | (SEQ ID NO: 2) |
| VRVSELGLGYASDET | (SEQ ID NO: 3) |
| LSVAELGLGYASEEK | (SEQ ID NO: 4) |
| IDFRKDLGWKWIHEPKG | (SEQ ID NO: 5) |
| IDFKRDLGWKWIHEPKG | (SEQ ID NO: 6) |
| IDFRQDLGWKWVHEPKG | (SEQ ID NO: 7) |
| IDLQGMKWAKNWVLEPPG | (SEQ ID NO: 8) |
| ETTYDKILKNLSRNR | (SEQ ID NO: 9) |
| RSPHDLSLASLLGAG | (SEQ ID NO: 10) |
| ARVYDLGLRRLRQRR | (SEQ ID NO: 11) |
| RTQHGLALARLQGQG | (SEQ ID NO: 12) |
| WSLDTQYSKVLALYN | (SEQ ID NO: 13) |
| WSSDTQHSRVLSLYN | (SEQ ID NO: 14) |
| RSADTTHSTVLGLYN. | (SEQ ID NO: 15) |
| DDLSFLDDNLVY | (SEQ ID NO: 16) |
| EAVSFMDVNSTW | (SEQ ID NO: 17) |
| DEVSFLDAHSRY | (SEQ ID NO: 18) |
| DVAFLDDRHRWQ. | (SEQ ID NO: 19) |
| EPLPIVYYVGRK | (SEQ ID NO: 20) |
| EPLTILYYIGKT | (SEQ ID NO: 21) |
| EPLTILYYVGRT. | (SEQ ID NO: 22) |

In some preferred embodiments the peptide may comprise one of the following sequences:

| | |
|---|---|
| LNVTDLGLGYETKEE | (SEQ ID NO: 1) |
| VPVRALGLGHRSDEL | (SEQ ID NO: 2) |
| VRVSELGLGYASDET | (SEQ ID NO: 3) |
| LSVAELGLGYASEEK, | (SEQ ID NO: 4) | or a fragment thereof.

In other preferred embodiments the peptide may comprise one of the following sequences:

| | |
|---|---|
| IDFRKDLGWKWIHEPKG | (SEQ ID NO: 5) |
| IDFKRDLGWKWIHEPKG | (SEQ ID NO: 6) |
| IDFRQDLGWKWVHEPKG | (SEQ ID NO: 7) |
| IDLQGMKWAKNWVLEPPG, | (SEQ ID NO: 8) | or a fragment thereof.

In still other preferred embodiments the fragment may comprise one of the following sequences:

| | |
|---|---|
| ETTYDKILKNLSRNR | (SEQ ID NO: 9) |
| RSPHDLSLASLLGAG | (SEQ ID NO: 10) |
| ARVYDLGLRRLRQRR | (SEQ ID NO: 11) |
| RTQHGLALARLQGQ, | (SEQ ID NO: 12) | or a fragment thereof.

In yet other preferred embodiments the fragment may comprise one of the following sequences:

| | |
|---|---|
| WSLDTQYSKVLALYN | (SEQ ID NO: 13) |
| WSSDTQHSRVLSLYN | (SEQ ID NO: 14) |
| RSADTTHSTVLGLYN, | (SEQ ID NO: 15) | or a fragment thereof.

In still yet other preferred embodiments the peptide may comprise one of the following sequences:

| | |
|---|---|
| DDLSFLDDNLVY | (SEQ ID NO: 16) |
| EAVSFMDVNSTWR | (SEQ ID NO: 17) |

```
DEVSFLDAHSRY         (SEQ ID NO: 18)
or

DVAFLDDRHRWQ,        (SEQ ID NO: 19)
or a fragment thereof.
```

Some embodiments may preferably concern the peptide which comprises one of the following sequences:

```
EPLPIVYYVGRK         (SEQ ID NO: 20)

EPLTI LYYIGKT        (SEQ ID NO: 21)
or

EPLTILYYVGRT,        (SEQ ID NO: 22)
or a fragment thereof.
```

In some preferred embodiments the invention concerns a peptide which comprises the sequences:

```
VPVRALGLGHRSDEL      (SEQ ID NO: 2)
VRVSELGLGYASDET      (SEQ ID NO: 3)
ETTYDKILKNLSRNR      (SEQ ID NO: 9)
RSPHDLSLASLLGAG      (SEQ ID NO: 10)
ARVYDLGLRRLRQRR      (SEQ ID NO: 11)
DDLSFLDDNLVY         (SEQ ID NO: 16)
EAVSFMDVNSTWR        (SEQ ID NO: 17)
DEVSFLDAHSRY         (SEQ ID NO: 18)
```

As already mentioned above, peptides of the invention encompasses 6 to 22 contiguous amino acid residues. However, the length of a peptide may be preferably selected, for example in the range of 6 to 10 amino acid residues, such as 7 to 9 amino acid residues, or in the range of 11 to 15 amino acid residues, such as for example 12 to 14 amino acid residues. The length of a peptide may also be in the range of 16 to 20 amino acid residues, for example 17 to 19 amino acid residues. It may also be of 21 or 22 amino acid residues.

For example, in one preferred embodiment the peptide may be a sequence of 18 amino acid residues. Then, a preferred 18 amino acid residues sequence of the invention is sequence IDLQGMKWAKNWVLEPPG (SEQ ID NO: 8).

In another preferred embodiment the peptide may be a sequence of 17 amino acid residues. In this case, a preferred 17 amino acid residues sequence may be selected from the following amino acid sequences:

```
IDFRKDLGWKWIHEPKG    (SEQ ID NO: 5)

IDFKRDLGWKWIHEPKG    (SEQ ID NO: 6)
or

IDFRQDLGWKWVHEPKG.   (SEQ ID NO: 7)
```

Still, in another preferred embodiment the peptide may be a sequence of 15 amino acid residues. Such sequence may be preferable selected from the following sequences:

```
LNVTDLGLGYETKEE      (SEQ ID NO: 1)
VPVRALGLGHRSDEL      (SEQ ID NO: 2)
VRVSELGLGYASDET      (SEQ ID NO: 3)
LSVAELGLGYASEEK      (SEQ ID NO: 4)
ETTYDKILKNLSRNR      (SEQ ID NO: 9)
RSPHDLSLASLLGAG      (SEQ ID NO: 10)
ARVYDLGLRRLRQRR      (SEQ ID NO: 11)
RTQHGLALARLQGQG      (SEQ ID NO: 12)
WSLDTQYSKVLALYN      (SEQ ID NO: 13)
WSSDTQHSRVLSLYN      (SEQ ID NO: 14)
or

RSADTTHSTVLGLYN.     (SEQ ID NO: 15)
```

Yet, in another preferred embodiment the peptide may be a sequence of 12 amino acid residues. Such peptide may be preferably selected form the following sequences:

```
DDLSFLDDNLVY         (SEQ ID NO: 16)
EAVSFMDVNSTWR        (SEQ ID NO: 17)
EVSFLDAHSRY          (SEQ ID NO: 18)
VAFLDDRHRWQ          (SEQ ID NO: 19)
EPLPIVYYVGRK         (SEQ ID NO: 20)
EPLTILYYIGKT         (SEQ ID NO: 21)
or

EPLTILYYVGRT.        (SEQ ID NO: 22)
```

Accordingly, a peptide consisting of any of the following sequences

```
LNVTDLGLGYETKEE      (SEQ ID NO: 1)
VPVRALGLGHRSDEL      (SEQ ID NO: 2)
VRVSELGLGYASDET      (SEQ ID NO: 3)
LSVAELGLGYASEEK      (SEQ ID NO: 4)
IDFRKDLGWKWIHEPK     (SEQ ID NO: 5)
IDFKRDLGWKWIHEPKG    (SEQ ID NO: 6)
IDFRQDLGWKWVHEPKG    (SEQ ID NO: 7)
IDLQGMKWAKNWVLEPPG   (SEQ ID NO: 8)
ETTYDKILKNLSRNR      (SEQ ID NO: 9)
RSPHDLSLASLLGAG      (SEQ ID NO: 10)
ARVYDLGLRRLRQRR      (SEQ ID NO: 11)
RTQHGLALARLQGQ       (SEQ ID NO: 12)
WSLDTQYSKVLALYN      (SEQ ID NO: 13)
WSSDTQHSRVLSLYN      (SEQ ID NO: 14)
RSADTTHSTVLGLYN      (SEQ ID NO: 15)
DDLSFLDDNLVY         (SEQ ID NO: 16)
EAVSFMDVNSTWR        (SEQ ID NO: 17)
DEVSFLDAHSRY         (SEQ ID NO: 18)
DVAFLDDRHRWQ.        (SEQ ID NO: 19)
```

```
EPLPIVYYVGRK            (SEQ ID NO: 20)

EPLTI LYYIGKT           (SEQ ID NO: 21)
or

EPLTILYYVGRT            (SEQ ID NO: 22)
``` is one of preferred embodiments of the invention.

In the present application the standard one-letter code for amino acid residues is applied as well as the standard three-letter code. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues, DAP, DAPA and 4Hyp.

Also, according to the invention modifications of the compounds/peptides may be performed, such as for example glycosylation and/or acetylation of the amino acids.

Basic amino acid residues are according to invention represented by the residues of amino acids Arg, Lys, and His, acidic amino acid residues—by the residues of amino acids Glu and Asp. Basic and amino acid residues constitute a group of charged amino acid residues. The group of hydrophobic amino acid residues is represented by the residues of amino acids Ala, Leu, Ile, Val, Phe, Trp, Tyr, and Met.

In one embodiment variants may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

The invention relates to naturally occurring, synthetically/recombinant prepared peptide sequence/fragments, and/or peptide sequence/fragments prepared by means of enzymatic/chemical cleavage of a bigger polypeptide, wherein said peptide sequence/fragments are integral parts of said bigger polypeptides. The invention relates to isolated individual peptide sequences.

The invention also related to variants of peptide sequences described above. In one aspect the term "variant of a peptide sequence" means that the peptides may be modified, for example by substitution of one or more of the amino acid residues. Both L-amino acids and D-amino acids may be used. Other modification may comprise derivatives such as esters, sugars, etc. Examples are methyl and acetyl esters.

In another aspect, variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

Other criteria for a variant of a peptide sequence are discussed below.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:
P, A, G (neutral, weakly hydrophobic),
S, T (neutral, hydrophilic)
Q, N (hydrophilic, acid amine)
E, D (hydrophilic, acidic)
H, K, R (hydrophilic, basic)
A, L, I, V, M, F, Y, W (hydrophobic, aromatic)
C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

As it was mentioned above the present invention relates to fragments, variant and homologues of the peptide sequences described above.

In the present context
i) a fragment is a sequence which has at least 40%, more preferably at least 50%, more preferably at least 60%, more preferably at least 70%, more preferably at least 80%, more preferably at least 90%, more preferably at least 95% of the length of a sequence corresponding to a sequence comprising the motif of the invention, in particular a sequence selected from the sequences of SEQ ID NOs: 1-22. It is preferred that a fragment of a sequence selected from the sequences of SEQ ID NOs: 1-22 comprises at least 4 amino acid residues of the motif $X_a$-(x)-$X_b$-$X_c$-$X_d$-$X_f$ which is described above, more preferably residues $X_b$-$X_c$-$X_d$-$X_f$ of said motif, such as for example sequences DLSFLDDNLVY (SEQ ID NO: 23), VSFMDVNSTWR (SEQ ID NO: 24), EVSFLDAHSRY (SEQ ID NO: 25) which are the fragments of sequences identified as SEQ ID NO; 16, 17 and 18 correspondingly;

ii) a variant is an amino acid sequence having at least 60%, more preferably at least 70%, more preferably at least 80%, more preferably at least 90%, more preferably 95% homology to a sequence comprising the motif of the invention, in particular to a sequence selected from the sequences of SEQ ID NOs: 1-22, or is an amino acid sequence having at least 60%, more preferably at least 70%, more preferably at least 80%, more preferably at least 90%, more preferably 95% positive amino acid matches compared to a sequence comprising the motif of the invention, in particular to a sequence of SEQ ID NOS: 1-22. A positive amino acid match is defined herein as an identity or similarity defined by physical and/or chemical properties of the amino acids having the same position in two compared sequences. Preferred positive amino acid matches of the present invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences. The homology of the sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90;

iii) a homologue is an amino acid sequence which has less then 60% but more then 30%, such as 50-59%, for example 55%, such as 40-49%, for example 45%, such as 30-39%, for example 35% homology to a sequence comprising the motif of the invention, in particular to a sequence of SEQ ID NOs: 1-22.

It is presumed that fragments, variants and homologues as defined above remain at least some biological activity of the original sequence, for example a capability of stimulating neural plasticity, such as associated with neural cell differentiation and/or such as associated with memory and learning, stimulating of cell survival, such as inhibiting apoptosis, activating the receptor of a protein which said original sequence is derived from.

As mentioned above, the invention relates both to naturally occurring, synthetically or recombinantly prepared peptides and peptides prepared by means of enzymatic/chemical cleavage of a bigger polypeptide sequence. The peptides produced by enzymatic cleavage of a bigger polypeptide sequence, as well as peptides, which are prepared by means of recombinant expression or by means of chemical synthesis, wherein said peptide sequences are corresponding to integral sequences of bigger polypeptides or proteins, are according to invention derived from the sequences of said bigger polypeptides or proteins.

The invention preferably relates to peptides derived from the sequences of the proteins belonging to the TGFbeta superfamily of proteins, in particular, GDNF, ARTN, NRTN, PSTN, TGFbeta-1, TGFbeta-2, TGFbeta-3 and TGFbeta-4.

Thus, in one embodiment a peptide of the invention may have or comprise a sequence corresponding to an integral sequence of glia-derived neurotrophic factor (GDNF). Such peptide according to the invention is derived from glia-derived neurotrophic factor (GDNF). Examples of the sequences derived from DGNF which meet the criteria for a peptide sequence of the invention are SEQ ID NOs: 1, 9 and 16.

A peptide according to the invention may have or comprise a peptide sequence derived from artemin (ARTN). Preferred ARTN-derived peptide sequences of the invention are identified herein as SEQ ID NOs: 2, 10 and 17. A peptide sequence may also derive from neurturin (NRTN) or persephin (PSTN). The sequences of the invention derived from NRTN and PSTN are identified herein as SEQ ID NOs: 3, 11 and 18 and SEQ ID NOs: 4, 12 and 19 correspondingly.

A peptide of the invention may comprise a sequence derived from transforming growth factor-beta-1 (TGFbeta-1), transforming growth factor-beta-2 (TGFbeta-2), transforming growth factor-beta-3 (TGFbeta-3) or transforming growth factor-beta-4 (TGFbeta-4), wherein preferred sequences derived from these proteins are identified herein as SEQ ID NOs: 5-8, 13-15 or 20-22 correspondingly.

According to the present invention an isolated peptide sequence as described above may be formulated as a compound, A compound may contain a single copy of an individual amino acid sequence selected from any of the described above, or it may contain two or more copies of such amino acid sequence. This means that compound of the invention may be formulated as a monomer of a peptide sequence, such as containing a single individual peptide sequence, or it may be formulated as a multimer of a peptide sequence, i.e containing two or more individual peptide sequences, wherein said individual peptide sequences may be represented by two or more copies of the same sequence or by two or more different individual peptide sequences. A multimer may also comprises a combination of the full-length sequence and one or more fragments thereof. In one embodiment a compound may contain two amino acid sequences, such compound is defined herein as dimer, in another embodiment a compound may contain more then two amino acid sequences, such for example three, four or more sequences. The present invention preferably relates to compounds containing two or four peptide sequences of the invention. However, compounds containing 3, 5, 6, 7, 8 or more sequences are also in the scope of the invention.

The peptide fragments formulated as dimers or multimers may have the identical amino acid sequences, or they may have different amino acid sequences. One example of such compound may be a compound containing SEQ ID NO: 1 and SEQ ID NO: 9. another example may be a compound containing SEQ ID NO: 1 and SEQ ID NO: 16. Any other combinations of the sequences of the invention may be made depending on different embodiments. The sequences may be connected to each other via peptide bond, or connected to each other through a linker molecule or grouping.

A compound of the invention may contain two or more identical copies of a sequence, such as for example two copies of a sequence selected from SEQ ID NOs: 1-22, wherein said two sequences may be connected to each other via a linker molecule or grouping. A compound wherein the sequences are connected via a linker grouping is preferred. One example of such linking grouping may be an achiral di-, tri- or tetracarboxylic acid. Suitable achiral di-, tri- or tetracarboxylic acids and a method of production such a compound (a ligand presentation assembly method (LPA)) are described in WO0018791 and WO2005014623. Another example of a possible linker may be the amino acid lysine. Individual peptide sequences may be attached to a core molecule such as lysine forming thereby a dendritic multimer (dendrimer) of an individual peptide sequence(s). Production of dendrimers is also well known in the art (PCT/US90/02039, Lu et al., (1991) Mol. Immunol. 28:623-630; Defoort et al., (1992) Int J Pept Prot Res. 40:214-221; Drijfhout et al. (1991) Int J Pept Prot Res. 37:27-32), and dedrimers are at present widely used in research and in medical applications. It is a preferred embodiment of the invention to provide a dendrimeric compound comprising four individual amino acid sequences attached to the lysine core molecule. It is also preferred that at least one of the four individual amino acid sequences comprises an amino acid sequence of the formula defined above. It is even more preferred if the all four individual amino acid sequences of a dendrimeric compound individually comprise an amino acid sequence of the formula defined above.

Multimeric compounds of the invention, such as LPA-dimers or Lysin-dendrmers, are preferred compounds of the invention. However, other types of multimeric compounds comprising two or more individual sequences of the invention may be preferred depending on the embodiments.

2. Biological Activity

A peptide sequence of the invention and a compound comprising a sequence of the invention possess biological activity. The invention preferably relates to a biological activity selected from capability of stimulating neural plasticity associated with neural cell differentiation, for example stimulating neurite outgrowth, capability neural plasticity associated with memory and learning, for example stimulating synaptic efficacy, capability of stimulating of cell survival, for example inhibiting apotosis, capability of inhibiting inflammation, such as stimulating anti-inflammatory response, capability of binding to a GDNF family receptor alfa (GFRalfa) and activating or inhibiting signal transduction, such as signal transduction associated with Ret receptor tyrosine kinase or associated with the neural cell adhesion molecule (NCAM), capability of binding to a component of a GFR/neural cell adhesion molecule (NCAM) complex. Thus, in one preferred embodiment a peptide according to the invention binds to NCAM.

Thus, in one embodiment an isolated peptide sequence as described above is capable of binding to GFRalfa receptor selected from GFRalfa-1, GFRalfa-2, GFRalfa-3 or GFRalfa-4.

The authors of the present invention has identified an amino acid motif which is present in a group of proteins belonging to the TGFbeta superfamily of proteins, in particular, proteins GDNF, ARTN, NRTN, PSTN, TGFbeta-1, TGFbeta-2, TGFbeta-3 and TGFbeta-4, and associated the presence of this motif with biological activity of said proteins and peptide fragments of the invention derived from thereof. The motif according to the invention is essential for binding of the peptide sequence of the invention to the receptor, in particular to GFRalfa receptor, even more particular to GFRalfa-1, GFRalfa-2, GFRalfa3 or GFRalfa4.

GFRalfa receptors are major receptors in the brain. GFRalfa receptors make a multicomponent receptor complex together with receptor tyrosine kinase Ret signalling through which drives differentiation of neural precursor cells, axonal growth, promotion of neuronal survival, neural plasticity associated with learning and memory particular. The capability of peptide sequences of the invention of binding and activating the GFRalfa-Ret or receptor complex serves to modulating biological responses dependent on activity of said receptor complexes. Accordingly, the invention provides a method of modulating activity of GFRalfa-Ret receptor complex comprising using an isolated peptide sequence of the invention or a compound comprising said sequence. In preferred embodiment, the invention relates to a method for activating GFRalfa receptor.

In another embodiment, an isolated peptide sequence as described above is capable of binding to GFRalfa-neural cell adhesion molecule (NCAM) receptor complex and activating or inhibiting thereby NCAM associated signal transduction.

NCAM plays a role a major cell adhesion molecule of neuronal cells which as at the same time a receptor-like molecule which associated with multiple intracellular signal transduction pathways in neuronal cells. It has recently been shown that GFRalfa receptor recruit NCAM in a signalling complex which is activated by GDNF binding to GFRalfa (Paratcha et al. (2003) Cell 113:867-879).

Thus, according to the invention an isolated peptide sequence of the invention is capable of stimulating neuronal cell differentiation through activating one of the GFNalfa receptor complexes described above. The term "neuronal differentiation" is understood herein both as differentiation of neural precursor cells, or neural stem cells, and further differentiation of neural cells, such as for example maturation of neuronal cells. An example of such differentiation may be neurite outgrowth from immature neurons, branching of neurites, and also neuron regeneration.

Thus, one preferred embodiment the invention concerns biological activity of a peptide sequence associated with stimulating of differentiation of neural precursor/stem cells or immature neurons, in another preferred embodiment the invention concern stimulating neurite outgrowth from mature neurons, for examples neurons which were traumatizes but survived and are committed to regenerate damaged processes. Accordingly, the invention also concerns a method for stimulating neuronal cell differentiation comprising using a peptide sequence of the invention or a compound comprising said sequence.

One of most preferred embodiments of the invention concerns the activity of the peptide sequences in connection with learning and memory, in particular, the capability of a peptide sequence to stimulate synaptic plasticity, spine formation, synaptic efficacy. Thus, the invention also concerns a method for stimulating memory and/or learning comprising using a peptide sequence of the invention and/or compound comprising said sequence. The invention relates to both short-term memory and long-term memory.

A peptide sequence of the invention may also stimulate neuronal cell survival. The invention concerns the capability of stimulating neuronal cell survival both due trauma and degenerative disease. Accordingly, the invention relates to a method for stimulating cell survival, preferably neuronal cell survival by using a peptide sequence of the invention and/or compound comprising said sequence.

In still another embodiment a peptide sequence of the invention may modulate cell adhesion, in particular NCAM-mediated cell adhesion. The term "modulating cell adhesion" includes both stimulating and inhibiting cell adhesion. This activity of a peptide sequence which influence a great number of processes in developing and adult neural system, and has a great relevance to a number of pathological conditions, for example cancer. Thus, a method for modulating cell adhesion, in particular NCAM-mediated cell adhesion, by using a peptide sequence of the invention or a compound comprising said sequence is also in the scope of the invention.

The peptide sequences of the invention and compounds comprising thereof are biologically active both as soluble/mobile substances of cell growth media and immobile substances of cell growth substrate. In some embodiments it may be preferred to use a peptide or a compound comprising thereof as a soluble substance, whereas in other embodiments it may be preferred to use a peptide sequences as cell substrate. However, soluble peptide sequences or compounds comprising thereof are more preferred.

In another embodiment the peptide sequence of the invention is also capable of inhibiting an inflammatory process, in particular an inflammatory process in the brain.

Inflammation is a defense reaction caused by tissue damage due to a mechanical injury or bacterial, virus or other organism infection. The inflammatory response involves three major stages: first, dilation of capillaries to increase blood flow; second, microvascular structural changes and escape of plasma proteins from the bloodstream; and third, leukocyte transmigration through endothelium and accumulation at the site of injury and infection. The inflammatory response begins with a release of inflammatory mediators. Inflammatory mediators are soluble, diffusible molecules that act locally at the site of tissue damage and infection, and at more distant sites, influencing consequent events of the inflammatory response. Inflammatory mediators can be exogenous, e.g. bacterial products or toxins, or endogenous, which are produced within the immune system itself, as well as injured tissue cells, lymphocytes, mast cells and blood proteins.

Neuroinflammation plays a prominent role in the progression of Alzheimer's disease and may be responsible for degeneration in vulnerable regions such as the hippocampus. Neuroinflammation is associated with elevated levels of extracellular glutamate and potentially an enhanced stimulation of glutamate N-methyl-D-aspartate receptors.

Anti-inflammatory is another important biological activity of the peptide sequence of the invention. Thus, the invention relates to anti-inflammatory peptide, which is capable of serving as an inhibitor of the sustained inflammatory response, in particular in the brain.

The continuous presence of inflammatory mediators, such as for example TNF alpha in the body in response to sustained presence of bacterial products or even live bacteria locally during days or weeks following trauma and/or infection promotes the reactions to inflammation, such as, for example, heat, swelling, and pain. The sustained inflammatory response has been proven to be very harmful to the body. If the bacterial products or live bacteria become spread universally in the body from their local focus the inflammatory reaction becomes overwhelming and out of control and leads to sepsis which eventually progress further to severe sepsis and septic shock. Anti-inflammatory peptides may be used to block or suppress the overwhelming sustained inflammatory response represented by a massive and harmful cytokine cascade in the blood and vital organs such as lung, liver intestine, brain and kidneys.

In the present context by the term "anti-inflammatory compound" is meant a compound which is capable of at least one of the following activities i) decreasing or inhibiting the gene expression in the immune cells, preferably monocytes/macrophages in response to bacterial products, live bacteria or trauma to produce endogenous inflammatory mediators including receptors for inflammatory mediators and transcription factors involved in the signal transduction of the inflammatory mediators, said mediators being preferably selected from the group comprising cytokines, selected from the group TNFalpha IL-1, IL-6, G-CSF, GM-CSF, M-CSF. Chemokines selected from the group comprising IL-8, MCP-1, receptors selected from the group Tissue factor and IL-2Ralpha, ii) decrease or inhibit the production bradykinin by the phase contact system,
iii) decrease or inhibit the attractant potential for monocytes, and/or
iv) decrease or inhibit the life-time of monocytes, neutrophils and other immune cells serving as an inducer of apoptosis,
v) decrease or inhibit vascular endothelial cells to express the adhesion molecules, said adhesion molecules being preferably selected from the group comprising PECAM, ICAM-1, E-selectins, VCAM-1
vi) decrease or inhibit activation of the contact phase system to produce bradykinin leading to increased vascular permeability,
vii) stimulate the synthesis of an anti-inflammatory mediator selected from the group of IL-10 and IL-12.
viii) inhibiting complement activation;
ix) decreasing the risk of neural cell degeneration in the presence of chronic neuroinflammation, e.g. neurons which express glutamate N-methyl-D-aspartate receptors.

One of non-limited examples of biological activity of the peptide sequences of the invention and compounds comprising thereof are described in the application below.

Stimulation of Neurite Outgrowth

Substances with the potential to promote neurite outgrowth as well as stimulate regeneration and/or differentiation of neuronal cells, such as certain endogenous trophic factors, are prime targets in the search for compounds that facilitate for example neuronal regeneration and other forms of neuronal plasticity. To evaluate the potential of the present compound, the ability to stimulate the neurite outgrowth related signalling, interfere with cell adhesion, stimulate neurite outgrowth, regeneration of nerves, may be investigated. Compounds of the present invention are shown to promote neurite outgrowth and are therefore considered to be good promoters of regeneration of neuronal connections, and thereby of functional recovery after damages as well as promoters of neuronal function in other conditions where such effect is required.

In the present context "differentiation" is related to the processes of maturation of neurons and extension of neurites, which take place after the last cell division of said neurons. The compounds of the present invention may be capable of stopping neural cell division and initiating maturation said cells, such as initiating extension of neurites. Otherwise, "differentiation" is related to initiation of the process of genetic, biochemical, morphological and physiological transformation of neuronal progenitor cells, immature neural cells or embryonic stem cells leading to formation of cells having functional characteristics of normal neuronal cell as such characteristics are defined in the art. The invention defines "immature neural cell" as a cell that has at least one feature of neural cell accepted in the art as a feature characteristic for the neural cell.

According to the present invention a compound comprising at least one of the above peptide sequences is capable of stimulating neurite outgrowth. The invention concerns the neurite outgrowth improvement/stimulation such as about 75% improvement/stimulation above the value of neurite outgrowth of control/non-stimulated cells, for example 50%, such as about 150%, for example 100%, such as about 250, for example 200%, such as about 350%, for example 300%, such as about 450%, for example 400%, such as about 500%.

Estimation of capability of a candidate compound to stimulate neurite outgrowth may be done by using any known method or assay for estimation of neurite outgrowth, such as for example as the described in Examples below.

According to the invention a compound has neuritogenic activity both as an insoluble immobile component of cell growth substrate and as a soluble component of cell growth media. In the present context "immobile" means that the compound is bound/attached to a substance which is insoluble in water or a water solution and thereby it becomes insoluble in such solution as well. For medical applications both insoluble and soluble compounds are considered by the application, however soluble compounds are preferred. Under "soluble compound" is understood a compound, which is soluble in water or a water solution.

Production of Individual Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell. Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4-c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 E1b region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

By SAPS peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality.

When synthesised, individual peptide sequences may then be formulated as multimers using well-known in the art techniques, for examples dimers of the sequences may be obtained by the LPA method described in WO 00/18791, denrimeric polymers by the MAP synthesis described in PCT/US90/02039.

Antibody

It is an objective of the present invention to provide an antibody, antigen binding fragment or recombinant protein thereof capable of recognizing and selectively binding to an epitope on GDNF, ARTN, NRTN, PSTN, TGFbeta-1, TGFbeta-2, TGFbeta-3 and/or TGFbeta-4, said epitope comprising the motif of the invention or a sequence selected from SEQ ID NOs:1-22, or a fragment of said sequence.

By the term "epitope" is meant the specific group of atoms (on an antigen molecule) that is recognized by (that antigen's) antibodies (thereby causing an immune response). The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta ($\delta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-22, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction.

(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The invention contemplate both polyclonal and monoclonal antibody, antigen binding fragments and recombinant proteins thereof which are capable of binding an epiyope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard method in the art for producing polyclonal and monoclonal antibodies using natural or recombinant fragments of human GDNF, ARTN, NRTN, PSTN, TGFbeta-1, TGFbeta-2, TGFbeta-3 and TGFbeta-4, said fragment comprising a sequence selected from SEQ ID NO: 1-22, as an antigen. Such antibodies may be also generated using variants, homologues or fragments of peptide sequences of SEQ ID NOs:1-22, said variants, homologues and fragments are immunogenic peptide sequences which meet the following criteria:
(i) being a contiguous amino acid sequence of at least 6 amino acids;
(ii) comprising the motif of the invention.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to antibodies, which are capable of modulating, such as enhancing or attenuating, biological function of GDNF, ARTN, NRTN, PSTN, TGFbeta-1, TGFbeta-2, TGFbeta-3 and TGFbeta-4, in particular a function related to neural cell differentiation, survival and/or plasticity, and to an antibody, which can recognise and specifically bind the latter proteins without modulating biological activity thereof.

The invention relates to use of the above antibodies for 1) therapeutic applications when the modulation of activity of human GDNF, ARTN, NRTN, PSTN, TGFbeta-1, TGFbeta-2, TGFbeta-3 and TGFbeta-4, is needed, 2) detecting and/or monitoring the latter proteins in vitro and/or in vivo for diagnostic purposes, 3) research purposes.

Pharmaceutical Composition

The invention also relates to a pharmaceutical composition comprising one or more of the compounds defined above, wherein the compound is capable of stimulating neurite outgrowth and/or neural cell differentiation, survival of neural cells and/or stimulating learning and/or memory. Thus, the invention concerns a pharmaceutical composition capable of stimulating differentiation of neuronal cells and/or stimulating regeneration of neuronal cells, and/or stimulating neuronal plasticity in connection with learning and memory, and/or stimulating survival of neural cells.

In the present context the term "pharmaceutical composition" is used synonymously with the term "medicament".

In a composition the peptide sequences may be formulated as comprising isolated individual peptide fragments or multimers or dimers thereof as discussed above.

The pharmaceutical composition may have the described above effects on cells in vitro or in vivo, wherein the composition is administered to a subject.

The medicament of the invention comprises an effective amount of one or more of the compounds as defined above, or a composition as defined above in combination with the pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, stimulating regeneration, plasticity and survival of neural cells in vitro or in vivo, said treatment involving administering an effective amount of one or more compounds as defined above.

Another strategy for administration is to implant or inject cells capable of expressing and secreting the compound in question. Thereby the compound may be produced at the location where it is going to act.

Treatment

In a further aspect, the present invention relates to said peptides, fragments, or variants thereof for use in the induction of differentiation and/or stimulation of regeneration, plasticity and/or survival of neural cells. The use is for the treatment for preventing diseases and conditions of the central and peripheral nervous system, and of the muscles or of various organs.

Treatment by the use of the compounds/compositions according to the invention is in one embodiment useful for inducing differentiation, modulating proliferation, stimulate regeneration, neuronal plasticity and survival of cells being implanted or transplanted. This is particularly useful when using compounds having a long term effect.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various or gans, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

In yet a further embodiment the use of the compound and/or pharmaceutical composition is for the stimulation of the ability to learn and/or of the short and/or long term memory.

In particular the compound and/or pharmaceutical composition of the invention may be used in the treatment of clinical conditions, such as psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nervesystem and sense organs, cognitive anomalies, inflammatory disease of the central nervous system, such as meningitis, encephalitis, Cerebral degenerations such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis; peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

Inflammation of the brain is often consequence of infection, autoimmune processes, toxins, and other conditions.

Viral infections are a relatively frequent cause of this condition. Encephalitis may occur as primary or secondary manifestation of TOGAVIRIDAE INFECTIONS; HERPESVIRIDAE INFECTIONS; ADENOVIRIDAE INFECTIONS; FLAVIVIRIDAE INFECTIONS; BUNYAVIRIDAE INFECTIONS; PICORNAVIRIDAE INFECTIONS; PARAMYXOVIRIDAE INFECTIONS; ORTHOMYXOVIRIDAE INFECTIONS; RETROVIRIDAE INFECTIONS; and ARENAVIRIDAE INFECTIONS.

Accordingly, a peptide, compound or a pharmaceutical composition of the invention may be used for treatment inflammation in the brain associated with a viral infection.

A large body of clinical and experimental data indicate that complement activation is an important mechanism for neuronal and glial injury in Guillain-Barré syndromes. Inhibition of complement activation therefore might be expected to limit the progression of the disease (Halstead et al. (2005) Annals of Neurology 58:203-21).

Thus, in another embodiment, a peptide sequence, a compound and pharmaceutical composition may be used for treatment of Guillain-Barré syndrome, its variant forms, such as Miller Fisher syndrome, and other complement dependent neuromuscular disorders.

Peptide sequences, compounds and pharmaceutical composition may also be used for treatment children with autism.

Autism is a brain disorder that begins in early childhood and persists throughout adulthood; affects three crucial areas of development: communication, social interaction, and creative or imaginative play. It is estimated to afflict between 2 and 5 of every 1000 children and is four times more likely to strike boys than girls. Children with autism have difficulties in social interaction and communication and may show repetitive behaviors and have unusual attachments to objects or routines.

In recent years, there have been scientific hints of immune system irregularities in children with autism.

Thus, a peptide sequence, compound or a composition comprising thereof may advantageously be used for treatment inflammation, in particular inflammation of the brain.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide. Thus, in a further aspect, the present invention relates to a prosthetic nerve guide, characterised in that it comprises one or more of the compounds or the pharmaceutical composition as defined above. Nerve guides are known in the art.

Another aspect of the invention relates to the use of a compound as defined above. In particular the use of a compound according to the invention is for the production of a pharmaceutical composition. The pharmaceutical composition is preferably for the treatment or prophylaxis of any of the diseases and conditions mentioned above.

In yet a further aspect the invention relates to a method of treating a disease or condition as discussed above by administering a compound as defined herein.

EXAMPLES

1. Effect of GDN, Artemin, and Neurturin Proteins and Peptide Fragments A1, A2, A3, G1, G2, G3, N1 and N2 Derived from These Proteins on Neuronal Cell Differentiation

| Peptides | | | |
|---|---|---|---|
| G1 | LNVTDLGLGYETKEE | (SEQ ID NO: 1) | GDNF fragment |
| A1 | VPVRALGLGHRSDEL | (SEQ ID NO: 2) | artemin fragment |
| N1 | VRVSELGLGYASDET | (SEQ ID NO: 3) | neurturin fragment |
| G2 | ETTYDKILKNLSRNR | (SEQ ID NO: 9) | GDNF fragment |
| A2 | RSPHDLSLASLLGAG | (SEQ ID NO: 10) | artemin fragment |
| N2 | ARVYDLGLRRLRQRR | (SEQ ID NO: 11) | neurturin fragment |
| G3 | DLSFLDDNLVY | (SEQ ID NO: 23) | GDNF fragment |
| A3 | VSFMDVNSTWR | (SEQ ID NO: 24) | artemin fragment |
| N3 | EVSFLDAHSRY | (SEQ ID NO: 25) | neurturin fragment |

Methods

Two different versions of the neurite outgrowth assay were used in this study, monocultures and co-cultures.

In monocultures, neurons are grown directly on plastic and the only neuritogenic stimulus is the one presented by the added substance. In co-cultures, neurons are grown on top of a confluent monolayer of fibroblasts expressing NCAM-140 (LBN110) or NCAM-negative control fibroblasts (LVN212). NCAM on the neurons interact with NCAM on LBN110 cells thereby stimulating neurite outgrowth from the neurons. This system thus permits the study of NCAM-NCAM interactions and interactions between NCAM and other molecules.

For all experiments cells were grown in neurobasal medium with supplements as described above in a final volume of 300 μl/well in 8-well LabTek® Permanox Chamber slides or 500 μl/well in 4-well LabTek® Permanox Chamber slides.

For monocultures, primary hippocampal neurons were seeded in 8-well LabTek® Permanox Chamber slides at a density of 10,000 cells/well.

For cocultures, L-cells were seeded in 8-well LabTek® Permanox Chamber slides at a density of 100.000 cells/well, except for transfection experiments where cells were seeded in 4-well LabTek® Permanox Chamber slides at a density of 200.000 cells/well. L-cells were grown for 24 hours in DMEM supplemented with 10% (v/v) FCS, 1% (v/v) glutamax, 100 U/ml penicillin, 100 μg/ml streptomycin, 2.5 μg/ml fungizone, and 567 μg/ml neomycin (G418), followed by washing twice in neurobasal medium with supplements before primary hippocampal neurons were seeded at a density of 7.000 cells/well in 8-well slides or 20.000 cells/well in 4-well slides.

To evaluate the effect peptides on neurite outgrowth, GDNF and the peptides, G1, G2, G3, A1, A2, A3, N1, N2 and N3 were diluted to the appropriate concentrations and added to the neurons approximately 10 minutes after seeding. Medium alone was added to controls, and cells were incubated for 24 hours.

To evaluate the involvement different intracellular signal transduction pathways pharmacological inhibitors, in particular the FGFR inhibitor SU5402 and Fyn-kinase inhibitor PP2, were diluted to the appropriate concentrations and added to the neurons immediately after seeding. After 10 minutes GDNF, GDNFp1 or medium (controls) was added and cells were incubated for 24 hours.

Additionally, neurons were transiently transfected with a dominant negative version of the FGFR (dnFGFR), As an alternative to the use of a pharmacological FGFR inhibitor, The dnFGFR plasmid encodes an FGFR that lacks the kinase domain. This mutant receptor inhibits the function of wild type FGFR by engaging in dimers that lack kinase activity. Transfection with an empty vector served as control. Transfection was also done with wtFGFR in order to assess the effect of overexpressing the FGFR.

To investigate the role of NCAM-180 and NCAM-140, respectively, transfections were carried out with plasmids encoding either the cytoplasmic domain of NCAM-180 or NCAM-140. The overexpressed cytoplasmic domains compete with the cytoplasmic domains of the endogenous NCAM molecules for cytoplasmic targets, probably functioning as inhibitors of NCAM-180 or NCAM-140 signalling. Transfection with an empty vector served as control.

Transfections were performed with a Nucleofector™ device and a Rat Neuron Nucleofector™ kit (Amaxa Inc., Gaithersburg, Md., USA). This transfection method is based on electroporation in combination with a Nucleofector™ solution containing lipophilic agents. These agents form liposomes containing the plasmid DNA, which then enter the cells during electroporation. The method allows transfection of undividing cells such as neurons. 3 μg of the plasmid of interest was mixed with the Nucleofector™ solution and primary hippocampal neurons were resuspended in the mixture, electroporated in the Nucleofector™ device, and transferred to neurobasal medium with supplements and 5% (v/v) FCS. Cells were then incubated for 2 hours after which they were resuspended in medium without serum, counted, seeded and incubated for 6 hours before GDNF or GDNFp1 was added. Medium alone was added to control and cells were incubated for 18 hours.

All transient transfections in this study included co-transfection with a plasmid encoding EGFP, which allows the identification of transfected cells. To ensure that all EGFP-expressing cells also are transfected with the plasmid of interest, a ratio of 1:5 between the EGFP-encoding plasmid and the plasmid of interest was used (i.e. 0.5 μg EGFP-encoding plasmid was used for each transfection).

Neurite outgrowth experiments were terminated after the stated time by fixating the cells. To visualize neurons and their neurites, immunostaining of GAP-43 was performed. This staining is specific for neurons. Transfected cells and their neurites should be visible without immunostaining due to the fluorescence emitted by GFP. In this study however, it was found that the intensity of GFP's own fluorescence was too weak to provide the image quality required for proper identification of transfected cells and analysis of neurite lengths. GFP is a cytoplasmic protein, and since thin neurites only contain a small volume of cytoplasm, GFP is only found in small amounts in most neurites. Therefore, a double-staining protocol, where cells were immunostained against GFP and GAP-43, was adopted. This protocol allowed the identification of transfected cells on the basis of GFP-staining in combination with visualization of neurites based on GAP-43-staining.

Without prior removal of the medium 300 μl/well (8-well slides) or 500 μl/well (4-well slides) of a PBS solution containing 0.4 mM $CaCl_2$, 0.05 M sucrose and 8% (v/v) formaldehyde was added to the cultures for 20 minutes. Cells were then washed 10 minutes in PBS followed by washing in PBS with 1% (w/v) BSA for 20 minutes, after which cells were incubated with primary antibodies overnight at 4° C.

Rabbit anti-rat GAP-43 antibodies were diluted 1:1000 for staining of untransfected cells and 1:2000 for staining of transfected cells. Mouse anti-GFP antibodies were diluted 1:1000. Antibodies were diluted in a PBS solution containing 7% (v/v) FCS to block unspecific binding, 50 mM glycine to block formaldehyde used for fixation, 0.2% (v/v) saponin to permeabilize cells, and 0.02% (v/v) $NaN_3$ to preserve antibodies for later use.

The next day cells were washed 10 minutes in PBS followed by washing in PBS with 1% (w/v) BSA for 20 minutes. Cells were then incubated with secondary antibodies diluted in PBS with 1% (w/v) BSA for one hour at room temperature. Goat anti-rabbit IgG antibodies conjugated to Alexa 488 were diluted 1:1000 for untransfected cells and 1:2000 for transfected cells. Goat anti-mouse IgG antibodies conjugated to Alexa 546 were diluted 1:1000. Finally cells were washed 3×7 minutes in PBS and mounted with fluorescent mounting medium.

Computer-assisted fluorescent microscopy was performed using a Nikon diaphot inverted microscope (Nikon, Tokyo, Japan) with a Nikon Plan 20× objective coupled to a video camera (Grundig Electronics Germany). For each condition in each experiment images of approximately 200 cells (untransfected cells) or 100 cells (transfected cells) were obtained in systematic series of fields of view, in which the position of the first image was chosen at random as described by Rønn et al. (2000c). This gives every cell an equal chance of being chosen. For each field of view of transfected cells GFP-staining was first recorded (green light) before switching the light to blue and recording GAP-43 staining. Light was then switched back before moving on to the next field of view.

Neurite outgrowth was analysed by counting the number of intersections between neurites and test lines in an unbiased counting frame using a software package "ProcessLength" developed at the Protein Laboratory (Rønn et al., 2000). Neurite outgrowth can then be quantified as the number of intersections per cell, which relates to the absolute length of neurites (L) per cell by the formula: $L=(\pi dI)/2$ (I=the number of intersections per cell, d=the vertical distance between two parallel lines in the frame).

Results

An important part of neuronal differentiation is the outgrowth of axons and dendrites, collectively known as neurites. The neurite outgrowth assay is thus an assay of neuronal differentiation, and is often used to test the neuritogenic potential of a given substance. In essence, neurons are grown for a certain time period in the presence of the molecule of interest, after which the outgrowth of neurites is quantified. Further, by the application of different inhibitors, the signal transduction mechanisms underlying the neuritogenic response seen can be investigated.

2. GDNF, Artemin, Neurturin Derived Peptides Effect on Neuronal Survival

Primary Cell Culture
Dopaminergic Neurons

Dopaminergic neurons were prepared from Wistar rat embryos at embryonic day 15 (Charles River, Sulzfeld, Germany or Møllegaard, Denmark). A pregnant rat was sacrificed and the uterus was taken out and kept on ice in Hank's balanced salt solution (HBSS; Gibco, BRL). The ventral part of the mesencephalon was dissected from the embryonic brains, homogenised on ice in Gey's balanced salt solution (GBSS; Gibco, BRL) supplemented with 5 g glucose/l (Sigma-Aldrich) and thereafter trypsinised. The dissociated cells were washed in the presence of DNAse 1 and soybean trypsin inhibitor (Sigma-Aldrich).

Cerebellar Granule Neurons

Cerebellar granule neurons (CGN) were prepared from postnatal day seven Wistar rats largely as previously described by Schousboe et al. (1989). Cerebellar tissue was dissected in modified Krebs-Ringer solution kept on ice, and treated as described for the hippocampal neurons above. All cell cultures were incubated at 37° C. in a humidified atmosphere containing 5% $CO_2$. All animals were handled in accordance with the national guidelines for animal welfare.

Survival Assay
Dopaminergic Neurons

Dopaminergic neurons were seeded at a density of 150,000 cells/cm² in 24-well cell culture plates coated with poly-D-lysine as described above. The neurons were left to differentiate for six days without or with various concentrations of peptide, after which 6-OHDA was added at a concentration of 100 µM for two hours. A stock solution was prepared by dissolving 6-OHDA to a concentration of 10 mM in 0.1% (w/v) sodium metabisulphite in order to prevent oxidation. After two hours with 6-OHDA, the medium was changed to Neurobasal medium with supplements and peptide, and the cell cultures were further incubated for 24 hours, fixed and immunostained for tyrosine hydroxylase. 98 images for each experimental condition in each individual experiment were automatically video-recorded.

Cerebellar Granule Neurons

Primary cultures of CGN were plated at a density of 100,000 cells/cm² on poly-L-lysine coated 8-well permanox slides in Neurobasal-A medium (Gibco, BRL) supplemented with 2% (v/v) B27, 0.5% (v/v) glutamax, 100 U/ml penicillin, 100 µg/ml streptomycin and KCl, making the final concentration of KCl in the medium 40 mM. 24 hours after plating, cytosine-β-D-arabinofuranoside (Ara-C; Sigma-Aldrich) was added to a final concentration of 10 µM to avoid proliferation of glial cells, after which the neurons were allowed to differentiate for further six days at 37° C. Apoptotic cell death was induced by washing twice and changing the medium to Basal Medium Eagle (BME; Gibco BRL) supplemented with 1% (v/v) glutamine, 100 U/ml penicillin and 100 µg/ml streptomycin, 3.5 g D-glucose/l and 1% (v/v) sodium pyruvate (Gibco BRL) together with various concentrations of peptide. Thereby the concentration of potassium in the cultures was reduced to 5 mM KCl (D'Mello et al., 1993). Two days after induction of apoptosis, the cells were fixed with 4% (v/v) formaldehyde and stained with Hoechst 33258 for 25 minutes as described by Kruman et al. (1997). Images of 1000-1500 neurons were randomly recorded for each group in each experiment using computer assisted fluorescence microscopy as described for the hippocampal neurite outgrowth assay. Nuclei from dead and live neurons were counted using the software package Prima developed at the Protein Laboratory, and the fraction of live neurons relative to the total number of neurons was estimated.

Results

Results are displayed and summarised in FIG. 25 and FIGS. 29 to 33.

3. Binding of GDNF, Artemin and Neurturin Derived Peptides to GFR and NCAM

Surface Plasmon Resonance (SPR) Analysis

Analysis of binding was performed employing a BIAcoreX instrument (Biosensor AB, Uppsala, Sweden) at 25° C. using 10 mM pH 7.4 sodium phosphate containing 150 mM NaCl as running buffer (phosphate-buffered saline, PBS). The flow-rate was 5 µl/min. Data were analysed by non-linear curve-fitting using the manufacturer's software. The receptor proteins, e.g. NCAM Ig1-Ig2 and GFR proteins, were immobilized on a sensor chip CM5 using an amine coupling kit (Biosensor AB) as follows: the chip was activated by 20 µl activation solution; the protein was immobilized using 12 µl 20 µg/ml protein in 10 mM sodium phosphate buffer pH 6.0; the chip was blocked by 35 µl blocking solution. Various peptides at the indicated concentrations were injected into the sensor chip. The curve corresponding to the difference between binding to receptor and a blank chip was used for analysis.

Results

Results are displayed and summarised in FIGS. 26 to 28 and FIGS. 34 to 38.

The invention claimed is:

1. A method of stimulating neurite outgrowth and/or increasing neuronal cell survival in a subject, comprising administering to said subject an effective amount of a compound which is a non-naturally occurring multimer comprising two or more peptides, which peptides may be the same or different, each peptide independently consisting of a sequence of 7 to 22 contiguous amino acid residues and comprising the formula (I):

$$X_a\text{-}(x)\text{-}X_b\text{-}X_c\text{-}X_d\text{-}X_f$$

wherein $X_a$ is amino acid residue D, E or A, (x) is a sequence of two amino acid residues selected from V-S, K-I, L-S and L-G $X_b$, is amino acid residue F, L or W, and at least one of $X_c$, $X_d$ or $X_f$ is a charged or hydrophobic amino acid residue, with the proviso that $X_f$ is not D or E, wherein said compound is not a homodimer consisting of two identical monomers in which the identical monomers are covalently linked by a disulfide bond, said compound being capable of stimulating neurite outgrowth or increasing neuronal cell survival.

2. The method according to claim 1, wherein $X_a$ is D.
3. The method according to claim 1, wherein $X_a$ is E.
4. The method according to claim 1, wherein $X_a$ is A.
5. The method according to claim 1, wherein at least one of $X_c$, $X_d$ or $X_f$ is a charged amino acid residue.
6. The method according to claim 1, wherein at least one of $X_c$, $X_d$ or $X_f$ is a hydrophobic amino acid residue.
7. The method according to claim 1, wherein at least one peptide
   (a) comprises an amino acid sequence selected from the sequences set forth in SEQ ID NOs: 2, 3, 9-11, and 16-18 or (b) is a fragment at least seven amino acids in length, of (a), or (c) comprises an amino acid sequence which differs from (a) solely by one or more conservative substitutions, or (d) comprises an amino acid sequence that differs from (a) solely by a single substitution.

8. The method according to claim 7, wherein at least one peptide comprises a sequence selected from the group consisting of

| | |
|---|---|
| LSVAELGLGYASEEK | (SEQ ID NO: 4) |
| IDFRKDLGWKWIHEPKG | (SEQ ID NO: 5) |
| IDFKRDLGWKWIHEPKG and | (SEQ ID NO: 6) |
| IDFRQDLGWKWVHEPKG. | (SEQ ID NO: 7) |

9. The method according to claim 1, wherein at least one peptide comprises SEQ ID NO:9.

10. The method according to claim 1, wherein at least one peptide comprises a sequence selected from the group consisting of the sequences of SEQ ID NOs: 2-7, 9-11 and 16-18.

11. The method according to claim 1, wherein said compound is capable of stimulating neural plasticity and/or inhibiting an inflammatory response.

12. The method of claim 1, wherein the multimer is a dendrimer.

13. The method of claim 1, which is a method of stimulating neurite outgrowth, said compound being capable of stimulating neurite outgrowth.

14. The method of claim 13, wherein said stimulating of neurite outgrowth is associated with stimulation of differentiation of neural precursor cells.

15. The method of claim 1, which is a method of increasing neuronal cell survival, said compound being capable of increasing neuronal cell survival.

16. The method of claim 1 wherein $X_c$ is not G.

17. The method of claim 1, wherein $X_b$ is L.

18. The method of claim 1, wherein at least one peptide has a length of at least 11 amino acid residues.

19. The method of claim 1 wherein (x) is L-G, K-I or L-S, $X_b$ is L or W, $X_c$ is G, K, A or R; $X_d$ is H, Y, N, S, R or W; and $X_f$ is R, A, L, I or V.

20. The method of claim 1, wherein at least one peptide has a length of at least 10 amino acid residues.

21. The method of claim 1, wherein at least one peptide has a length of at least 15 amino acid residues.

22. The method of claim 1, wherein at least one peptide comprises an amino acid sequence of the formula $$X_a\text{-}(x)\text{-}X_b\text{-}X_c\text{-}X_d\text{-}X_f\text{-}x^8\text{-}x^9\text{-}x^{10}$$

Wherein $X_c$ is an amino acid residue selected from the group consisting of G, K, M, A, R, L, S, F or I, $X_d$ is an amino acid residue selected from the group consisting of Y, H, W, K, N, S, R, A, M, L, D or V, $X_f$ is an amino acid residue selected from the group consisting of R, A, I, V, W, L, or Y, $x^8$ is an amino acid residue selected from the group consisting of T, S, H, L, R, D, V, A and Y, $x^9$ is an amino acid residue selected from the group consisting of K, D, E, R, G, Q, A, S, N, H, V and I, and $x^{10}$ is an amino acid residue selected from the group consisting of E, P, N, A, R, G, L and S.

23. The method of claim 1, wherein (x) is a sequence of two amino acid residues selected from K-I, L-S and L-G and $X_b$ is amino acid residue L or W.

24. The method of claim 1 wherein $X_b$ is L; (x) is L-G, K-I or L-S; $X_c$ is G, K, A or R; $X_d$ is H, Y, N, S, or R; and $X_f$ is R, A, or L.

25. The method of claim 1 wherein $X_c$ is G, K, A, R, L or M; $X_d$ is H, Y, N, S, R, W, or D; and $X_f$ is R, A, L, I, or V.

26. The method of claim 1 wherein at least one said peptide comprises an amino acid sequence selected from the group consisting of SEQ ID NOS: 2, 3, 5-7, and 9-11.

27. The method of claim 1 wherein at least one said peptide comprises an amino acid sequence selected from the group consisting of SEQ ID NOs: 2, 3, and 9-11.

28. The method of claim 1 wherein at least one said peptide comprises an amino acid sequence selected from the group consisting of SEQ ID NOs: 2, 3, 5-7, 9-11 and 16-18.

29. The method of claim 1 wherein the multimer comprises not less than 2 and not more than 8 sequences satisfying formula (I).

30. The method of claim 1 wherein the multimer comprises not less than 2 and not more than 4 sequences satisfying formula (I).

31. The method of claim 1 wherein the multimer comprises 2 and only 2 sequences satisfying formula (I).

32. The method of claim 1 wherein Xf is R, A, L, I or W.

33. The method of claim 32 wherein said multimer (a) comprises at least two identical heptapeptide sequences satisfying formula (I), or (b) at least two of said peptides are connected to each other by a peptide bond, by a dendrimer lysine core moiety, or by a linker that is not a peptide bond, an amino acid, a sequence of contiguous amino acids, or a disulfide bond.

34. The method of claim 32 wherein in said multimer of (b), at least two of said peptides are connected to each other by a peptide bond, a dendrimeric lysine core moiety, or an achiral di-, tri- or tetracarboxylic acid linker.

35. The method of claim 32, wherein (x) is a sequence of two amino acid residues selected from K-I, L-S and L-G, $X_b$ is amino acid residue L or W, and Xf is R, A or L.

36. The method of claim 1 wherein (i) Xf is a hydrophobic residue or (ii) Xf is R.

37. The method of claim 36 wherein said multimer (a) comprises at least two identical heptapeptide sequences satisfying formula (I), or (b) at least two of said peptides are connected to each other by a peptide bond, by a dendrimer lysine core moiety, or by a linker that is not a peptide bond, an amino acid, a sequence of contiguous amino acids, or a disulfide bond.

38. The method of claim 36 wherein in said multimer of (b), at least two of said peptides are connected to each other by a peptide bond, a dendrimeric lysine core moiety, or an achiral di-, tri- or tetracarboxylic acid linker.

39. The method of claim 1 wherein said multimer (a) comprises at least two identical heptapeptide sequences satisfying formula (I), or (b) at least two of said peptides are connected to each other by a peptide bond, by a dendrimer lysine core moiety, or by a linker that is not a peptide bond, an amino acid, a sequence of contiguous amino acids, or a disulfide bond.

40. The method of claim 39 wherein in said multimer of (b), at least two of said peptides are connected to each other by a peptide bond, a dendrimeric lysine core moiety, or an achiral di-, tri- or tetracarboxylic acid linker.

41. The method of claim 1 wherein the multimer comprises 4 and only 4 sequences satisfying formula (I).

42. The method according to claim 1 wherein at least one peptide comprises SEQ ID NO:2.

43. The method according to claim 1 wherein at least one peptide comprises SEQ ID NO:3.

44. The method according to claim 1 wherein at least one peptide comprises SEQ ID NO:10.

45. The method according to claim 1 wherein at least one peptide comprises SEQ ID NO:11.

46. The method according to claim 1 wherein at least one peptide comprises SEQ ID NO:16.

47. The method according to claim 1 wherein at least one peptide comprises SEQ ID NO:17.

48. The method according to claim 1 wherein at least one peptide comprises SEQ ID NO:18.

49. A method of stimulating neurite outgrowth and/or increasing neuronal cell survival in a subject, comprising administering to said subject an effective amount of a compound which is a non-naturally occurring multimer comprising two or more peptides, which peptides may be the same or different, each independently consisting of a sequence of 7 to 22 contiguous amino acid residues and comprising the formula (I):

$$X_a\text{-}(x)\text{-}X_b\text{-}X_c\text{-}X_d\text{-}X_f$$

wherein
$X_a$ is amino acid residue D, E or A,
(x) is a sequence of two amino acid residues selected from V-S, K-I, L-S and L-G,
$X_b$ is amino acid residue F, L or W, and
at least one of $X_c$, $X_d$ or $X_f$ is a charged or hydrophobic amino acid residue, with the proviso that $X_f$ is not D or E,
wherein said multimer comprises not more than 176 amino acid residues, not counting any dendrimeric lysine core,
said compound being capable of stimulating neurite outgrowth or increasing neuronal cell survival.

50. The method of claim 49 wherein said multimer comprises not more than 88 amino acid residues, not counting any dendrimeric lysine core.

51. A method of stimulating neurite outgrowth and/or increasing neuronal cell survival and/or binding to a GFRa receptor in a subject, comprising administering to said subject an effective amount of a compound which is a non-naturally occurring multimer comprising two or more peptides, which peptides may be the same or different, each peptide independently consisting of a sequence of 7 to 22 contiguous amino acid residues and comprising the formula (I):

$$X_a\text{-}(x)\text{-}X_b\text{-}X_c\text{-}X_d\text{-}X_f$$

wherein
$X_a$ is amino acid residue D, E or A,
(x) is a sequence of two amino acid residues selected from V-S, K-I, L-S and L-G,
$X_b$ is amino acid residue F, L or W, and
at least one of $X_c$, $X_d$ or $X_f$ is a charged or hydrophobic amino acid residue, with the proviso that $X_f$ is not D or E,
wherein said compound is not a homodimer consisting of two identical monomers in which the identical monomers are covalently linked by a disulfide bond,
said compound being capable of stimulating neurite outgrowth or increasing neuronal cell survival or binding to a GFRa receptor.

52. The method of claim 51, wherein (x) is a sequence of two amino acid residues selected from K-I, L-S and L-G and $X_b$ is amino acid residue L or W.

* * * * *